United States Patent
Ghayer et al.

(10) Patent No.: US 7,767,207 B2
(45) Date of Patent: Aug. 3, 2010

(54) ANTIBODIES THAT BIND IL-18 AND METHODS OF INHIBITING IL-18 ACTIVITY

(75) Inventors: Tariq Ghayer, Holliston, MA (US); Richard W. Dixon, Jefferson, MA (US); Michael Roguska, Ashland, MA (US); Michael White, Framingham, MA (US); Boris Labkovsky, Marlborough, MA (US); Jochen Salfeld, North Grafton, MA (US); Alexander Robert Duncan, Little Shelford (GB); Simon Mark Brocklehurst, Fulbourn (GB); John Mankovich, Andover, MA (US); Celia Patricia Shorrock, Cambridge (GB); Julia Elizabeth Thompson, Whittlesford (GB); Simon Nicholas Lennard, Linton (GB)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/780,035

(22) Filed: Feb. 9, 2001

(65) Prior Publication Data

US 2010/0104563 A1   Apr. 29, 2010

Related U.S. Application Data

(60) Provisional application No. 60/181,608, filed on Feb. 10, 2000.

(51) Int. Cl.
*A61K 39/395* (2006.01)
*C07K 16/24* (2006.01)

(52) U.S. Cl. .............. 424/145.1; 424/130.1; 424/133.1; 424/158.1; 530/387.1; 530/387.3; 530/388.15; 530/388.23

(58) Field of Classification Search .............. 424/85.1, 424/85.2, 130.1, 133.1, 135.1, 141.1, 142.1, 424/145.1, 152.1, 153.1, 158.1, 172.1, 173.1; 530/350, 351, 387.1, 387.3, 382.9, 388.1, 530/388.15, 388.2, 388.23, 388.7, 388.73
See application file for complete search history.

(56) References Cited

U.S. PATENT DOCUMENTS

| 5,060,283 | A |  | 10/1991 | Shiraishi et al. |
| 5,545,806 | A |  | 8/1996 | Lonberg et al. |
| 5,545,807 | A |  | 8/1996 | Surani et al. |
| 5,597,669 | A |  | 1/1997 | Hamada et al. |
| 5,612,205 | A |  | 3/1997 | Kay et al. |
| 5,625,126 | A |  | 4/1997 | Lonberg et al. |
| 5,625,825 | A |  | 4/1997 | Rostoker et al. |
| 5,627,052 | A |  | 5/1997 | Schrader et al. |
| 5,633,425 | A |  | 5/1997 | Lonberg et al. |
| 5,643,763 | A |  | 7/1997 | Dunn et al. |
| 5,661,016 | A |  | 8/1997 | Lonberg et al. |
| 5,721,367 | A |  | 2/1998 | Kay et al. |
| 5,770,429 | A |  | 6/1998 | Lonberg et al. |
| 5,789,215 | A |  | 8/1998 | Berns et al. |
| 5,789,650 | A |  | 8/1998 | Lonberg et al. |
| 5,814,318 | A |  | 9/1998 | Lonberg et al. |
| 5,849,500 | A |  | 12/1998 | Breitlinger et al. |
| 5,912,324 | A |  | 6/1999 | Okamura et al. |
| 5,916,771 | A |  | 6/1999 | Hori et al. |
| 5,939,598 | A |  | 8/1999 | Kucherlapati et al. |
| 5,985,615 | A |  | 11/1999 | Jakobovits et al. |
| 5,994,619 | A |  | 11/1999 | Stice et al. |
| 5,998,209 | A |  | 12/1999 | Jakobovits et al. |
| 6,054,487 | A |  | 4/2000 | Sekut et al. |
| 6,075,181 | A | * | 6/2000 | Kucherlapati et al. |
| 6,091,001 | A |  | 7/2000 | Jakobovits et al. |
| 6,114,598 | A |  | 9/2000 | Kucherlapati et al. |
| 6,130,364 | A |  | 10/2000 | Jakobovits et al. |
| 6,140,470 | A | * | 10/2000 | Garen et al. |
| 6,309,636 | B1 |  | 10/2001 | doCouto et al. |
| 7,135,458 | B1 |  | 11/2006 | Ushio et al. |

FOREIGN PATENT DOCUMENTS

| EP | 0850952 | 7/1998 |
| EP | 0864585 | 9/1998 |
| EP | 0962531 | 12/1999 |

(Continued)

OTHER PUBLICATIONS

Bendig Methods: A Companion to Methods in Enzymology 1995; 8:83-93.*
Ward et al. Nature 1989; 341:544-546.*
Riechmann and Muyldermans J. Immunol. Meth. 1999; 231:25-38.*
Rudikoff et al., PNAS 79: 1979-1983, 1982.*
Panka et al., PNAS 85: 3080-3084, 1988.*
Brown et al. Anti-Tac-H, a humanized antibody to the interleukin 2 receptor, prolongs primate cardiac allograft survival. *Proc. Natl. Acad. Sci.* (1991) 88:2663-2667.
Dinarello, C. et al. Overview of interleukin-18: more than an interferon-gamma inducing factor. *J. Leukoc. Biol.* (1998) 63:658-664.
Dinarello, C.A. IL-18: a TH1-inducing, proinflammatory cytokine and new member of the IL-1 family. *J. Allergy Clin. Immunol.* (1999), 103(1, Pt. 1), pp. 11-24.

(Continued)

*Primary Examiner*—Phillip Gambel
(74) *Attorney, Agent, or Firm*—McCarter & English, LLP; Maria Laccotripe Zacharakis; Maneesh Gulati

(57) ABSTRACT

Antibodies that bind human interleukin-18 (hIL-18) are provided, in particular antibodies that bind epitope(s) of human IL-18. The antibodies can be, for example, entirely human antibodies, recombinant antibodies, or monoclonal antibodies. Preferred antibodies have high affinity for hIL-18 and neutralize hIL-18 activity in vitro and in vivo. An antibody of the invention can be a full-length antibody or an antigen-binding portion thereof. Method of making and method of using the antibodies of the invention are also provided. The antibodies, or antibody portions, of the invention are useful for detecting hIL-18 and for inhibiting hIL-18 activity, e.g., in a human subject suffering from a disorder in which hIL-18 activity is detrimental.

16 Claims, 5 Drawing Sheets

FOREIGN PATENT DOCUMENTS

| | | |
|---|---|---|
| EP | 974 600 A2 | 1/2000 |
| EP | 0712931 | 2/2001 |
| WO | WO 91/10741 | 7/1991 |
| WO | WO 91/17271 | 11/1991 |
| WO | WO 92/01047 | 1/1992 |
| WO | WO 92/02551 | 2/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 94/02602 | 2/1994 |
| WO | WO 96/33735 | 10/1996 |
| WO | WO 96/34096 | 10/1996 |
| WO | WO 97/24441 | 7/1997 |
| WO | WO 97/29131 | 8/1997 |
| WO | WO 97/44468 | 11/1997 |
| WO | WO 98/16654 | 4/1998 |
| WO | WO 98/24893 | 6/1998 |
| WO | WO 98/41232 | 9/1998 |
| WO | WO 98/50433 | 11/1998 |
| WO | WO 99/09063 | 2/1999 |
| WO | WO 99/22760 | 5/1999 |
| WO | WO 99/25044 | 5/1999 |
| WO | WO 99/37772 | 7/1999 |
| WO | WO 99/37773 | 7/1999 |
| WO | WO 99/45031 | 9/1999 |
| WO | WO 99/53049 | 10/1999 |
| WO | WO 00/09560 | 2/2000 |
| WO | WO 00/12555 | 3/2000 |
| WO | WO 00/37504 | 6/2000 |
| WO | WO 00/56771 A1 | 9/2000 |
| WO | WO 00/56772 | 9/2000 |
| WO | WO 00/75348 | 12/2000 |
| WO | WO 01/07480 | 1/2001 |
| WO | WO 01/58956 | 8/2001 |
| WO | WO 01/81423 | 11/2001 |
| WO | WO 01/83525 | 11/2001 |
| WO | WO 02/60479 | 8/2002 |
| WO | WO 02/72636 | 9/2002 |

OTHER PUBLICATIONS

Fantuzzi, G. and Dinarello, C.A. Interleukin-18 and interleukin-1beta: two cytokine substrates for ICE (caspase-1). *J. Clin. Immunol.* (1999), 19(1), pp. 1-11.

Hooft, R.W. et al., Errors in Protein Structures. *Nature* (1996) 381, pp. 272.

Kohka, H. et al., Involvement of interleukin-18 (IL-18) in mixed lymphocyte reactions (MLR) *J. Interferon Cytokine Res.* (1999) 19(9), pp. 1053-1057.

Priestle, J., et al. The three-dimensional structure of human interleukin-1.beta. refined to 2.0 .ANG. resolution. *Prog. Clin. Biol. Res.* (1990), 349 (Cytokines Lipocortins Inflammation Differ.), pp. 297-307.

Sali, A. et al., Evaluation of comparative protein modeling by MODELLER. *Proteins: Struct., Funct., Genet.* (1995), 23(3), pp. 318-326. CODEN: PSFGEY; ISSN: 0887-3585.

Schreuder, H. et al., Refined crystal structure of the interleukin-1 receptor antagonist: presence of a disulfide link and a cis-proline. *Eur. J. Biochem.* (1995), 227(3), pp. 838-847.

Vigers, G., et al. Crystal structure of the type-I interleukin-1-receptor complexed with interleukin-1.beta. *Nature* (London) (1997), 386(6621), pp. 190-194.

Adachi O., et al., Targeted Disruption of the MyD88 Gene Results in Loss of IL-1- and IL-18-Mediated Function, Immunity, (1998), vol. 9, pp. 143-150.

Akita Kenji, et al, Involvement of Capse- and Capase -3 in the Production and Processing of Mature Human Interleukin 18 in Monocytic THP.1 Cells, The Journal of Biological Chemistry, (1997) vol. 272(42), pp. 26595-26603.

Alberts, Bruce et al., The Cell 4th Edition, Garland Science, p. 161 figs 3-42.

Babcock, John S. et al., A novem Strategy for generating monoclonal antibodies from single, isolated lymphocytes producing antibodies of defined specificities, Proc. Natl. Acad. Sci, (1996), vol. 93, pp. 7843-7848.

Balint, Robert F., et al., Antibody engineering by parsimonious mutagenesis, Gene. (1993) vol. 137, pp. 109-118.

Barbas, Carlos F., III., et al., Assembly of combinatorial antibody libraries on phage surfaces: The gene site, Proc. Natl. Acad. Sci, (1991), vol. 88, pp. 7978-7982 .

Bendele, Alison et al., Animal Models of Arthritis: Revelance to Human Disease, Toxicology Pathology, (1999) vol. 27(1), pp. 134-142.

Bird, Robert E. et al., Single-Chain Antigen-Binding Proteins, Science (1988), vol. 242, pp. 423-426.

Clackson, Tim et al., Making Antibody fragments using phage display libraries, Letters to Nature, (1991), vol. 352, pp. 624-628.

Davies, Julian et al., Affinity improvement of single antibody VH domains: residues in all three hypervariable regions afect antigen binding, Immunotechnology 2 (1996), pp. 169-179.

Dinarello, C, Interleukin-18, Methods (1999), vol. 19, pp. 121-132.

Fassbender, K., MD., et al., Interferon-y-inducing factor (IL-18) and interferon-y in inflammatory CNS diseases, Neurology, (1999) vol. 53, pp. 1104-1106.

Fuchs, Patrick, et al., Targeting Recombinant Antibodies to the Surface of Escherichis Coli: Fusion to a Peptidoglycan Associated Lipoprotein, Bio/Technology (1991) vol. 9, pp. 1370-1372.

Garrad, Lisa J. et al., FAB Assembly and Enrichment in a Monovalent Phage Display System, Bio-Technology (1991) vol. 9 pp. 1373-1377.

Gavilondo, Jorge V., et al., Antibody Engineering at the Millenium, Bio Techniques (2000) vol. 29, pp. 128-145.

Ghayur, Tariq et al., Caspase-1 processes IFN-y-inducing factor and regulates LPS-induced IFN-y productions, Nature (1997) vol. 386, pp. 619-623.

Ghetie, Victor et al., Increasing the serum persistence of an IgG fragment by random mutagenesis, Nature Biotechnology, (1997) vol. 15, pp. 637-640.

Giege, Richard et al., Crystallization of Nucleic Acids and Proteins, A Practical Approach, 2nd Edition (1999), pp. 1-16.

Gram, Hermann et al., Invitro selection and affinity maturation of antibodies from a naive combinatorial immunoglobulin library, Biochemistry (1992) vol. 89, pp. 3576-3580.

Green, L.L. et al., Antigen-specific human monoclonal antibodies from mice engineered with human Ig heavy and light chain YACs, Nature Genetics (1994) vol. 7, pp. 13-21.

Green, Larry L. et al., Regulation of B Cell Development by Variable Gene Complexity in Mice Reconstituted with Human Immunoglobulin Yeast Artificial Chromosomes, J. Exp. Med. (1998), vol. 188, pp. 483-495.

Griffiths, Andrew D. et al., Human anti-self antibodies with high specifity from phage display libraries, the EMBO Journal (1993), vol. 12(2), pp. 725-734.

Gu, Yong et al., Activation of Interferon-y Inducing Factor mediated by Interleukin-1B Converting Enzyme, Science (1997), vol. 275, pp. 206-209.

Hawkins, Robert E. et al., Selection of Phage Antibodies by Binding Affinity mimicking Maturation, J. Mol. Biol. (1992), vol. 226, pp. 889-896.

Hay, Beverly N., et al., Bacteriophage cloning and *Eschericia coli* expression of human IgM Fab, Human Antibody Hybridomas, (1992), vol. 3, pp. 81-85.

Hezareh, Marjan et al., Effector Function Activities of a Panel of Mutants of a Broadly Neutralizing Antibody against Human Immuno deficiency Virus Type 1, Journal of Virology (2001), vol. 75(24), pp. 12161-12168.

Holliger, Phillip et al., "Diabodies": Small bivalent and bispecific antibody fragments, Biophysics (1993), vol. 90, pp. 6444-6448.

Hoogenboom, Hennie R., et al., Multi-subunit proteins on the surface of filamentous phage: methodologies for displaying antibody (Fab) heavy and light chains, Nucleic Acids Research, (1991) vol. 19(15), pp. 4133-4137.

Hoogenboom, Hennie R. et al., Natural and Designer binding sites made by phage display technology, Immunology Today (2000) vol. 21, pp. 371-378.

Hoogenboom, Hennie R., Designing and optimizing library selection strategies for generating high-affinity antibodies, TIB Tech., (1997) vol. 15, pgsl 62-70.

Hoshino, Katsuaki et al, Cutting Edge: Generation of IL-18 Receptor-Deficient Mice: Evidence for IL-1 Receptor-Related Protein as an essential IL-18 Binding Receptor, Journal of Immunology, (1999) vol. 162, pp. 5041-5044.

Huston, James S. et al, Protein engineering of antibody binding sites: Recovery of specific activity in an anti-digoxin single chain Fv analogue produced in *Escherichia coli,* Proc. Natl. Acad. Sci., (1988) vol. 85, pp. 5879-5883.

Huse, William D. et al., Generation of a Large Combinatorial Library of Immunoglobulin Repertoire in Phage Lambda, Science, (1989) vol. 246, pp. 1275-1281.

Johnsson, Bo et al., Immobilization fo Proteins to a Carboxymethyldextran Modified Gold Surface for Biospecific Interation Analysis in Surface Plasmon Resonance Sensors, Analytical Biochemistry, (1991) vol. 198, pp. 268-277.

Johnsson, Bo et al, Comparison of Methods for Immobilization ot Carvoxymethyl Dextran Snsor Suraces by Analysis of the Specific Activity of Monoclonal Antibodies, Journal of Molecular Recognition (1995), vol. 8, pp. 125-131.

Jonsson, U et al., Introducing a biosensor based technology for real-time biospefici interation anaylsis, Ann. Bio. Clin., (1993) vol. 51, pp. 19-26.

Jonsson, U et al., Real-Time Biospecific Interaction Analysis Using Surface Plasmon Resonance and a Sensor Chip Technology, Biotechniques, (1991) vol. 11, pp. 620-627.

Junghans, R.P. et al., Anti-Tac-H, a Humanized Antibody to the Interleukin 2 Receptor with New Features for Immunotherapy in Malignant and Immune Disorders, Cancer Research (1990) vol. 50, pp. 1495-1502.

Kanakaraj, Palanisamy et al., Defective Interleukin IL-18-mediated Natural Killer and T Helper Cell Type 1 Responses in IL-1 Receptor-associated Kinase (IRAK)-deficient Mice, J. Exp. Med., (1999) vol. 189, pp. 1129-1138.

Kaufmann, Randal J. et al., Amplification and Expression of Sequences Cotransfected with a Molecular Dihydrofolate Reductase Complementary DNA Gene, J. Mol. Bio, (1982) vol. 159, pp. 601-621.

Kearney, John F. et al., A New Mouse Myeloma Cell Line That Has Lost Immunoglobulins Expression but Permits the construction of Antibody-Secreting Hybrid Cell Lines, The Journal of Immunology (1979) vol. 123, pp. 1548-1550.

Kettleborough, Catherine A. et al., Humanization of a mouse monoclonal antibody by CDR-grafting: the importance of framework residues on loop conformation, Protein Engineering, (1991) vol. 4, pp. 773-783.

Kim, Jin-Kyoo et al, Maping the site on human IgG for binding of the MHC class I-related receptor, FcRn, Eur. J. of Immunology, (1999), vol. 29, pp. 2819-2825.

Kipriyanov, Sergey M. et al., Single-chain antibody streptavidin fusions: Tetrameric bifunctional ScFv-complexes with biotin binding activity and enhanced affinity to antigen, Human Antivody and Hybridomas (1995), vol. 6(3), pp. 93-101.

Konishi, Kaori et al., A simple and sensative bioassay for the detection of human interleukin-18/interferon-y-inducing factor using human myelomonocytic KG-1 cells, Journal of Immunological methods (1997), vol. 209, pp. 187-191.

Leung, Bernard P. et al., A Role for IL-18 in Neutrophil Activation, The Journal of Immunology (2001), vol. 167, pp. 2879-2886.

Little, M. et al., Of mice and men: hybridoma and recombinant antibodies, Immunology Today (2000), vol. 21, pp. 364-370.

Lonberg, Nils et al., Antigen-specific human antibodies from mice comprising four distinct genetic modifications, Letters to Nature (1994), vol. 368, pp. 856-859.

Lund, John et al., Human FcyRI and FcyRII With Distinct but Overlapping Sites on human IgG, The Journal of Immunology (1991), vol. 147(8), pp. 2657-2662.

McCafferty, John et al., Phage Antibodies: filamentous phage displaying antibody variable domains, Letters to Nature (1990), vol. 348, pp. 552-554.

Taylor, Lisa D. et al., A transgenic mouse that expresses a diversity of human sequence heavy and light chain immun, Nucleic Acids Research (1992), vol. 20(23), pp. 6287-6295.

Tissi, Luciana et al., Role of Tumor Necrosis Factor Alpha, Interleukin-1B and Interleukin-6 in a mouse model of Group B , Infection and Immunity (1999), vol. 67; 4545-4550.

Trentham, David E. et al., Autoimmunity to Type II Collage: An Experimental Model of Arthritis, Journal of Exp. Med. (1977) vol. 146, pp. 857-868.

Tsutsui, Hiroko et al, Caspase-1 Independent, Fas/Fas/ Ligand-Mediated IL-18 Secretion from Macrophages Cases Acute liver injury in Mice, Immunity (1999) vol. 11, pp. 359-367.

Tsutsui, Hiroko et al., IL-18 Accounts for both TNF-a- and Fas Ligand-Mediated Hpatotoxic Pathways, Jour. of Immun., (1997), vol. 159(8) pp. 3961-3967.

Urlaub Gail et al., Isolation of Chinese hamster cell mutants deficient in dihydrofolate reductase activity, Pro. Natl. Acad. Sci. (1980) vol. 77(7), pp. 4216-4220.

Ushio Shimpei et al., Cloning of the cDNA for Human IFN-y-Inducing Factor, Expression in *Escherichia coli,* Journal of Immunology (1996) vol. 156, pp. 4274-4279.

Van Nostrand, William E. et al., Protease nexin-II, a potent antichymotrypsin, shows identity to amyloid B-protein precursor, Nature (1989) vol. 341, pp. 546-551.

Wildbaum, Gizi et al., Neutralizing Antibodies to IF-y-inducing Factor Prevent Experimental Autoimmune Encephalomyelitis, Journ. of Immun. (1998) vol. 161(11), pp. 6368-6374.

Winter, Greg et al., Making Antibodies by Phage Display Technology, Annua. Rev. of Immun. (1994), vol. 12, pp. 433-455.

McInnes, Iain B. et al., Interleukin 18: a pleiotropic participant in chronic inflammation, Immunology Today (2000) vol. 21, pp. 312-315.

Mendez, Michael J. et al., Functional transplant of megabase human immunoglobulin loci recapitulates human antibody response in mice, Nature Genetics (1997), vol. 15; 146-156.

Mizushima, Seiichi et al., pEF-BOS, a powerful mammalian expression vector, Nucleic Acids Research, (1990) vol. 18(17), p. 5322.

Monteleone, Giovanni et al., Bioactive IL-18 Expression is up-Regulated in Chron's Disease, Journal of Immunology, (1999) vol. 163(1), pp. 143-147.

Netea, Mihai G. et al., Neutralization of IL-18 Reduces Neutrophil Tissue Accumulation, The Journal of Immunology (2000) vol. 164, pp. 2644-2649.

Poljak, Roberto J., Production and Structure of diabodies, Structure (1994) , vol. 2, pp. 1121-1123.

Queen, Cary et al., A human antibody that binds to the interleukin 2 receptor, Proc. Natl. Acad. Sci., (1989) vol. 86, pp. 10029-10033.

Reichmann, Lutz et al., Reshaping human antibodies for therapy, Nature (1988), vol. 332, pp. 323-327.

Takeda, Kiyoshi et al., Defective Nk Cell Activity and Th1 Response in IL-18 Deficient Mice, Immunity (1998) vol. 8, pp. 383-390.

Taniguchi, Mutsuko et al., Characterization of anti-human interleukin-18 (IL-18), Journal of Immun. Methods (1997) vol. 206; 107-113.

* cited by examiner

IL-1β    IL-18    IL-1RA

SEQUENCE LISTING

<160> NUMBER OF SEQ ID NOS: 71

<210> SEQ ID NO 1
<211> LENGTH: 15
<212> TYPE: PRT
<213> ORGANISM: Homo sapiens

<400> SEQUENCE: 1

Pro Leu Phe Glu Asp Met Thr Asp Ser Asp Cys Arg Asp Asn Ala
 1               5                  10                  15

<210> SEQ ID NO 2
<211> LENGTH: 16
<212> TYPE: PRT
<213> ORGANISM: Homo sapiens

<400> SEQUENCE: 2

Cys Pro Leu Phe Glu Asp Met Thr Asp Ser Asp Cys Arg Asp Asn Ala
 1               5                  10                  15

<210> SEQ ID NO 3
<211> LENGTH: 12
<212> TYPE: PRT
<213> ORGANISM: Homo sapiens

<400> SEQUENCE: 3

Pro Leu Phe Glu Asp Met Thr Asp Ser Asp Cys Arg
 1               5                  10

<210> SEQ ID NO 4
<211> LENGTH: 157
<212> TYPE: PRT
<213> ORGANISM: Homo sapiens

<400> SEQUENCE: 4

Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 5
<211> LENGTH: 153
<212> TYPE: PRT
<213> ORGANISM: Homo sapiens

<400> SEQUENCE: 5

Ala Pro Val Arg Ser Leu Asn Cys Thr Leu Arg Asp Ser Gln Gln Lys
 1               5                  10                  15

Ser Leu Val Met Ser Gly Pro Tyr Glu Leu Lys Ala Leu His Leu Gln
            20                  25                  30

Gly Gln Asp Met Glu Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

```
Glu Ser Ala Gln Phe Pro Asn Trp Tyr Ile Ser Thr Ser Gln Ala Glu
            115                 120                 125

Asn Met Pro Val Phe Leu Gly Gly Thr Lys Gly Gly Gln Asp Ile Thr
        130                 135                 140

Asp Phe Thr Met Gln Phe Val Ser Ser
145                 150
```

<210> SEQ ID NO 6
<211> LENGTH: 145
<212> TYPE: PRT
<213> ORGANISM: Homo sapiens

<400> SEQUENCE: 6

```
Ser Ser Lys Met Gln Ala Phe Arg Ile Trp Asp Val Asn Gln Lys Thr
  1               5                  10                  15

Phe Tyr Leu Arg Asn Asn Gln Leu Val Ala Gly Tyr Leu Gln Gly Pro
             20                  25                  30

Asn Val Asn Leu Glu Glu Lys Ile Asp Val Val Pro Ile Glu Pro His
         35                  40                  45

Ala Leu Phe Leu Gly Ile His Gly Gly Lys Met Cys Leu Ser Cys Val
     50                  55                  60

Lys Ser Gly Asp Glu Thr Arg Leu Gln Leu Glu Ala Val Asn Ile Thr
 65                  70                  75                  80

Asp Leu Ser Glu Asn Arg Lys Gln Asp Lys Arg Phe Ala Phe Ile Arg
                 85                  90                  95

Ser Asp Ser Gly Pro Thr Thr Ser Phe Glu Ser Ala Ala Cys Pro Gly
            100                 105                 110

Trp Phe Leu Cys Thr Ala Met Glu Ala Asp Gln Pro Val Ser Leu Thr
        115                 120                 125

Asn Met Pro Asp Glu Gly Val Met Val Thr Lys Phe Tyr Phe Gln Glu
    130                 135                 140

Asp
145
```

<210> SEQ ID NO 7
<211> LENGTH: 297
<212> TYPE: PRT
<213> ORGANISM: Homo sapiens

<400> SEQUENCE: 7

```
Cys Thr Ser Arg Pro His Ile Thr Val Val Glu Gly Glu Pro Phe Tyr
  1               5                  10                  15

Leu Lys His Cys Ser Cys Ser Leu Ala His Glu Ile Glu Thr Thr Thr
             20                  25                  30

Lys Ser Trp Tyr Lys Ser Ser Gly Ser Gln Glu His Val Glu Leu Asn
         35                  40                  45

Pro Arg Ser Ser Ser Arg Ile Ala Leu His Asp Cys Val Leu Glu Phe
     50                  55                  60

Trp Pro Val Glu Leu Asn Asp Thr Gly Ser Tyr Phe Phe Gln Met Lys
 65                  70                  75                  80

Asn Tyr Thr Gln Lys Trp Lys Leu Asn Val Ile Arg Arg Asn Lys His
                 85                  90                  95

Ser Cys Phe Thr Glu Arg Gln Val Thr Ser Lys Ile Val Glu Val Lys
            100                 105                 110

Lys Phe Phe Gln Ile Thr Cys Glu Asn Ser Tyr Tyr Gln Thr Leu Val
        115                 120                 125
```

-continued

```
Asn Ser Thr Ser Leu Tyr Lys Asn Cys Lys Lys Leu Leu Glu Asn
    130                 135                 140

Asn Lys Asn Pro Thr Ile Lys Lys Asn Ala Glu Phe Glu Asp Gln Gly
145                 150                 155                 160

Tyr Tyr Ser Cys Val His Phe Leu His His Asn Gly Lys Leu Phe Asn
                165                 170                 175

Ile Thr Lys Thr Phe Asn Ile Thr Ile Val Glu Asp Arg Ser Asn Ile
            180                 185                 190

Val Pro Val Leu Leu Gly Pro Lys Leu Asn His Val Ala Val Glu Leu
        195                 200                 205

Gly Lys Asn Val Arg Leu Asn Cys Ser Ala Leu Leu Asn Glu Glu Asp
    210                 215                 220

Val Ile Tyr Trp Met Phe Gly Glu Glu Asn Gly Ser Asp Pro Asn Ile
225                 230                 235                 240

His Glu Glu Lys Glu Met Arg Ile Met Thr Pro Glu Gly Lys Trp His
                245                 250                 255

Ala Ser Lys Val Leu Arg Ile Glu Asn Ile Gly Glu Ser Asn Leu Asn
            260                 265                 270

Val Leu Tyr Asn Cys Thr Val Ala Ser Thr Gly Gly Thr Asp Thr Lys
        275                 280                 285

Ser Phe Ile Leu Val Arg Lys Ala Asp
    290                 295

<210> SEQ ID NO 8
<211> LENGTH: 310
<212> TYPE: PRT
<213> ORGANISM: Homo sapiens

<400> SEQUENCE: 8

Cys Lys Glu Arg Glu Glu Lys Ile Ile Leu Val Ser Ser Ala Asn Glu
  1               5                  10                  15

Ile Asp Val Arg Pro Cys Pro Leu Asn Pro Asn Glu His Lys Gly Thr
            20                  25                  30

Ile Thr Trp Tyr Lys Asp Asp Ser Lys Thr Pro Val Ser Thr Glu Gln
        35                  40                  45

Ala Ser Arg Ile His Gln His Lys Glu Lys Leu Trp Phe Val Pro Ala
    50                  55                  60

Lys Val Glu Asp Ser Gly His Tyr Tyr Cys Val Val Arg Asn Ser Ser
65                  70                  75                  80

Tyr Cys Leu Arg Ile Lys Ile Ser Ala Lys Phe Val Glu Asn Glu Pro
                85                  90                  95

Asn Leu Cys Tyr Asn Ala Gln Ala Ile Phe Lys Gln Lys Leu Pro Val
            100                 105                 110

Ala Gly Asp Gly Gly Leu Val Cys Pro Tyr Met Glu Phe Phe Lys Asn
        115                 120                 125

Glu Asn Asn Glu Leu Pro Lys Leu Gln Trp Tyr Lys Asp Cys Lys Pro
    130                 135                 140

Leu Leu Leu Asp Asn Ile His Phe Ser Gly Val Lys Asp Arg Leu Ile
145                 150                 155                 160

Val Met Asn Val Ala Glu Lys His Arg Gly Asn Tyr Thr Cys His Ala
                165                 170                 175

Ser Tyr Thr Tyr Leu Gly Lys Gln Tyr Pro Ile Thr Arg Val Ile Glu
            180                 185                 190

Phe Ile Thr Leu Glu Glu Asn Lys Pro Thr Arg Pro Val Ile Val Ser
        195                 200                 205
```

-continued

```
Pro Ala Asn Glu Thr Met Glu Val Asp Leu Gly Ser Gln Ile Gln Leu
    210                 215                 220

Ile Cys Asn Val Thr Gly Gln Leu Ser Asp Ile Ala Tyr Trp Lys Trp
225                 230                 235                 240

Asn Gly Ser Val Ile Asp Glu Asp Pro Val Leu Gly Glu Asp Tyr
                245                 250                 255

Tyr Ser Val Glu Asn Pro Ala Asn Lys Arg Arg Ser Thr Leu Ile Thr
                260                 265                 270

Val Leu Asn Ile Ser Glu Ile Glu Ser Arg Phe Tyr Lys His Pro Phe
            275                 280                 285

Thr Cys Phe Ala Lys Asn Thr His Gly Ile Asp Ala Ala Tyr Ile Gln
        290                 295                 300

Leu Ile Tyr Pro Val Thr
305                 310

<210> SEQ ID NO 9
<211> LENGTH: 6
<212> TYPE: PRT
<213> ORGANISM: Homo sapiens

<400> SEQUENCE: 9

Thr Gly Tyr Tyr Ile His
1               5

<210> SEQ ID NO 10
<211> LENGTH: 17
<212> TYPE: PRT
<213> ORGANISM: Homo sapiens

<400> SEQUENCE: 10

Gly Arg Leu Asn Pro Thr Thr Gly Asp Ala Asn Phe Ala Glu Lys Phe
1               5                   10                  15

Gln

<210> SEQ ID NO 11
<211> LENGTH: 4
<212> TYPE: PRT
<213> ORGANISM: Homo sapiens

<400> SEQUENCE: 11

Lys Glu Gly Ala
1

<210> SEQ ID NO 12
<211> LENGTH: 11
<212> TYPE: PRT
<213> ORGANISM: Homo sapiens

<400> SEQUENCE: 12

Gln Gly Asp Ser Leu Arg His Phe Tyr Pro Asn
1               5                   10

<210> SEQ ID NO 13
<211> LENGTH: 7
<212> TYPE: PRT
<213> ORGANISM: Homo sapiens

<400> SEQUENCE: 13

Gly Lys Asn Asn Arg Pro Ser
1               5
```

```
<210> SEQ ID NO 14
<211> LENGTH: 11
<212> TYPE: PRT
<213> ORGANISM: Homo sapiens

<400> SEQUENCE: 14

Gly Ser Arg Asp Ser Ser Gly Ile His Val Val
 1               5                  10

<210> SEQ ID NO 15
<211> LENGTH: 11
<212> TYPE: PRT
<213> ORGANISM: Homo sapiens

<400> SEQUENCE: 15

Gln Gly Asp Ser Leu Arg His Phe Tyr Ser Asn
 1               5                  10

<210> SEQ ID NO 16
<211> LENGTH: 17
<212> TYPE: PRT
<213> ORGANISM: Homo sapiens

<400> SEQUENCE: 16

Gly Arg Leu Asn Pro Arg Thr Gly Asp Ala Asn Phe Ala Glu Lys Phe
 1               5                  10                  15

Gln

<210> SEQ ID NO 17
<211> LENGTH: 17
<212> TYPE: PRT
<213> ORGANISM: Homo sapiens

<400> SEQUENCE: 17

Gly Arg Leu Asn Pro Arg Thr Gly Asp Ala Gln Phe Ala Glu Lys Phe
 1               5                  10                  15

Gln

<210> SEQ ID NO 18
<211> LENGTH: 113
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
 1               5                  10                  15

Ser Met Lys Val Ser Cys Lys Thr Ser Gly Tyr Thr Phe Thr Gly Tyr
                20                  25                  30

Tyr Ile His Trp Val Arg Gln Ala His Gly Gln Gly Phe Glu Trp Ile
            35                  40                  45

Gly Arg Leu Asn Pro Thr Thr Gly Asp Ala Asn Phe Ala Glu Lys Phe
        50                  55                  60

Gln Gly Arg Val Ala Leu Thr Arg Asp Thr Ser Ile Ser Thr Ala Tyr
 65                  70                  75                  80

Leu Gln Leu Asp Ser Leu Lys Ser Asp Asp Thr Ala Val Tyr Tyr Cys
                85                  90                  95

Ala Gly Lys Glu Gly Ala Trp Gly Gln Gly Thr Leu Val Thr Val Ser
            100                 105                 110

Ser
```

```
<210> SEQ ID NO 19
<211> LENGTH: 109
<212> TYPE: PRT
<213> ORGANISM: Homo sapiens

<400> SEQUENCE: 19

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg His Phe Tyr Pro
             20                  25                  30

Asn Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60

Gly Ser Gly Asn Thr Gly Ser Leu Thr Ile Thr Gly Ala Gln Ala Glu
 65                  70                  75                  80

Asp Glu Ala Asp Tyr Tyr Cys Gly Ser Arg Asp Ser Ser Gly Ile His
                 85                  90                  95

Val Val Phe Gly Gly Gly Thr Lys Val Thr Val Leu Gly
            100                 105

<210> SEQ ID NO 20
<211> LENGTH: 4
<212> TYPE: PRT
<213> ORGANISM: Homo sapiens

<400> SEQUENCE: 20

Ser Tyr Ala Met
 1

<210> SEQ ID NO 21
<211> LENGTH: 17
<212> TYPE: PRT
<213> ORGANISM: Homo sapiens

<400> SEQUENCE: 21

Ala Ile Ser Gly Ser Gly Gly Ser Thr Tyr Tyr Ala Asp Ser Val Lys
 1               5                  10                  15

Gly

<210> SEQ ID NO 22
<211> LENGTH: 9
<212> TYPE: PRT
<213> ORGANISM: Homo sapiens

<400> SEQUENCE: 22

Asp Asp Asp Asp Tyr Asp Phe Asp Tyr
 1               5

<210> SEQ ID NO 23
<211> LENGTH: 13
<212> TYPE: PRT
<213> ORGANISM: Homo sapiens

<400> SEQUENCE: 23

Ser Gly Ser Ser Ser Asn Ile Gly Ile Asn Ala Val Asn
 1               5                  10

<210> SEQ ID NO 24
<211> LENGTH: 6
<212> TYPE: PRT
```

```
<213> ORGANISM: Homo sapiens

<400> SEQUENCE: 24

Gly Asn Asp Gln Arg Pro
  1               5

<210> SEQ ID NO 25
<211> LENGTH: 11
<212> TYPE: PRT
<213> ORGANISM: Homo sapiens

<400> SEQUENCE: 25

Ala Ala Trp Asp Asp Ser Leu Ser Gly Pro Val
  1               5                  10

<210> SEQ ID NO 26
<211> LENGTH: 17
<212> TYPE: PRT
<213> ORGANISM: Homo sapiens

<400> SEQUENCE: 26

Ala Ile Ser Gly Ser Gln Gly Ser Thr Tyr Tyr Ala Asp Ser Val Lys
  1               5                  10                  15

Gly

<210> SEQ ID NO 27
<211> LENGTH: 17
<212> TYPE: PRT
<213> ORGANISM: Homo sapiens

<400> SEQUENCE: 27

Ala Ile Ser Gly Ser Gly Gly Ser Thr Trp Tyr Ala Asp Ser Val Lys
  1               5                  10                  15

Gly

<210> SEQ ID NO 28
<211> LENGTH: 108
<212> TYPE: PRT
<213> ORGANISM: Homo sapiens

<400> SEQUENCE: 28

Leu Val Gln Pro Gly Gly Ser Leu Arg Leu Ser Cys Ala Ala Ser Gly
  1               5                  10                  15

Phe Thr Phe Ser Ser Tyr Ala Met Ser Trp Val Arg Gln Ala Pro Gly
                 20                  25                  30

Lys Gly Leu Glu Trp Val Ser Ala Ile Ser Gly Ser Gly Gly Ser Thr
             35                  40                  45

Tyr Tyr Ala Asp Ser Val Lys Gly Arg Phe Thr Ile Ser Arg Asp Asn
         50                  55                  60

Ser Lys Asn Thr Leu Tyr Leu Gln Met Asn Ser Leu Arg Ala Glu Asp
 65                  70                  75                  80

Thr Ala Val Tyr Tyr Cys Ala Arg Asp Asp Asp Tyr Asp Phe Asp
                 85                  90                  95

Tyr Trp Gly Arg Gly Thr Met Val Thr Val Ser Ser
            100                 105

<210> SEQ ID NO 29
<211> LENGTH: 111
<212> TYPE: PRT
<213> ORGANISM: Homo sapiens
```

<400> SEQUENCE: 29

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ile Asn
            20                  25                  30

Ala Val Asn Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Gly Pro Val Phe Gly Gly Gly Thr Lys Leu Thr Val Leu Gly
            100                 105                 110

<210> SEQ ID NO 30
<211> LENGTH: 235
<212> TYPE: PRT
<213> ORGANISM: Homo sapiens

<400> SEQUENCE: 30

Leu Val Gln Pro Gly Gly Ser Leu Arg Leu Ser Cys Ala Ala Ser Gly
1               5                   10                  15

Phe Thr Phe Ser Ser Tyr Ala Met Ser Trp Val Arg Gln Ala Pro Gly
            20                  25                  30

Lys Gly Leu Glu Trp Val Ser Ala Ile Ser Gly Ser Gly Gly Ser Thr
        35                  40                  45

Tyr Tyr Ala Asp Ser Val Lys Gly Arg Phe Thr Ile Ser Arg Asp Asn
    50                  55                  60

Ser Lys Asn Thr Leu Tyr Leu Gln Met Asn Ser Leu Arg Ala Glu Asp
65                  70                  75                  80

Thr Ala Val Tyr Tyr Cys Ala Arg Asp Asp Asp Tyr Asp Phe Asp
                85                  90                  95

Tyr Trp Gly Arg Gly Thr Met Val Thr Val Ser Ser Gly Gly Gly Gly
            100                 105                 110

Ser Gly Gly Gly Gly Ser Gly Gly Gly Ser Ala Gln Ser Val Leu
        115                 120                 125

Thr Gln Pro Pro Ser Ala Ser Gly Thr Pro Gln Arg Val Thr Ile
    130                 135                 140

Ser Cys Ser Gly Ser Ser Asn Ile Gly Ile Asn Ala Val Asn Trp
145                 150                 155                 160

Tyr Gln Gln Leu Pro Gly Thr Ala Pro Lys Leu Leu Ile Tyr Gly Asn
                165                 170                 175

Asp Gln Arg Pro Ser Gly Val Pro Asp Arg Phe Ser Gly Ser Lys Ser
            180                 185                 190

Gly Thr Ser Ala Ser Leu Ala Ile Ser Gly Leu Gln Ser Glu Asp Glu
        195                 200                 205

Ala Asp Tyr Tyr Cys Ala Ala Trp Asp Asp Ser Leu Ser Gly Pro Val
    210                 215                 220

Phe Gly Gly Gly Thr Lys Leu Thr Val Leu Gly
225                 230                 235

<210> SEQ ID NO 31
<211> LENGTH: 14

```
<212> TYPE: PRT
<213> ORGANISM: Homo sapiens

<400> SEQUENCE: 31

Tyr Phe Gly Lys Leu Glu Ser Lys Leu Ser Val Ile Arg Asn
 1               5                  10

<210> SEQ ID NO 32
<211> LENGTH: 14
<212> TYPE: PRT
<213> ORGANISM: Homo sapiens

<400> SEQUENCE: 32

Glu Ser Lys Leu Ser Val Ile Arg Asn Leu Asn Asp Gln Val
 1               5                  10

<210> SEQ ID NO 33
<211> LENGTH: 14
<212> TYPE: PRT
<213> ORGANISM: Homo sapiens

<400> SEQUENCE: 33

Val Ile Arg Asn Leu Asn Asp Gln Val Leu Phe Ile Asp Gln
 1               5                  10

<210> SEQ ID NO 34
<211> LENGTH: 14
<212> TYPE: PRT
<213> ORGANISM: Homo sapiens

<400> SEQUENCE: 34

Asn Asp Gln Val Leu Phe Ile Asp Gln Gly Asn Arg Pro Leu
 1               5                  10

<210> SEQ ID NO 35
<211> LENGTH: 14
<212> TYPE: PRT
<213> ORGANISM: Homo sapiens

<400> SEQUENCE: 35

Phe Ile Asp Gln Gly Asn Arg Pro Leu Phe Glu Asp Met Thr
 1               5                  10

<210> SEQ ID NO 36
<211> LENGTH: 14
<212> TYPE: PRT
<213> ORGANISM: Homo sapiens

<400> SEQUENCE: 36

Asn Arg Pro Leu Phe Glu Asp Met Thr Asp Ser Asp Cys Arg
 1               5                  10

<210> SEQ ID NO 37
<211> LENGTH: 14
<212> TYPE: PRT
<213> ORGANISM: Homo sapiens

<400> SEQUENCE: 37

Glu Asp Met Thr Asp Ser Asp Cys Arg Asp Asn Ala Pro Arg
 1               5                  10

<210> SEQ ID NO 38
<211> LENGTH: 14
<212> TYPE: PRT
<213> ORGANISM: Homo sapiens
```

<400> SEQUENCE: 38

Ser Asp Cys Arg Asp Asn Ala Pro Arg Thr Ile Phe Ile Ile
1               5                   10

<210> SEQ ID NO 39
<211> LENGTH: 14
<212> TYPE: PRT
<213> ORGANISM: Homo sapiens

<400> SEQUENCE: 39

Asn Ala Pro Arg Thr Ile Phe Ile Ile Ser Met Tyr Lys Asp
1               5                   10

<210> SEQ ID NO 40
<211> LENGTH: 14
<212> TYPE: PRT
<213> ORGANISM: Homo sapiens

<400> SEQUENCE: 40

Ile Phe Ile Ile Ser Met Tyr Lys Asp Ser Gln Pro Arg Gly
1               5                   10

<210> SEQ ID NO 41
<211> LENGTH: 14
<212> TYPE: PRT
<213> ORGANISM: Homo sapiens

<400> SEQUENCE: 41

Met Tyr Lys Asp Ser Gln Pro Arg Gly Met Ala Val Thr Ile
1               5                   10

<210> SEQ ID NO 42
<211> LENGTH: 14
<212> TYPE: PRT
<213> ORGANISM: Homo sapiens

<400> SEQUENCE: 42

Gln Pro Arg Gly Met Ala Val Thr Ile Ser Val Lys Cys Glu
1               5                   10

<210> SEQ ID NO 43
<211> LENGTH: 14
<212> TYPE: PRT
<213> ORGANISM: Homo sapiens

<400> SEQUENCE: 43

Ala Val Thr Ile Ser Val Lys Cys Glu Lys Ile Ser Thr Leu
1               5                   10

<210> SEQ ID NO 44
<211> LENGTH: 14
<212> TYPE: PRT
<213> ORGANISM: Homo sapiens

<400> SEQUENCE: 44

Val Lys Cys Glu Lys Ile Ser Thr Leu Ser Cys Glu Asn Lys
1               5                   10

<210> SEQ ID NO 45
<211> LENGTH: 14
<212> TYPE: PRT
<213> ORGANISM: Homo sapiens

<400> SEQUENCE: 45

```
Ile Ser Thr Leu Ser Cys Glu Asn Lys Ile Ile Ser Phe Lys
 1               5                   10
```

<210> SEQ ID NO 46
<211> LENGTH: 14
<212> TYPE: PRT
<213> ORGANISM: Homo sapiens

<400> SEQUENCE: 46

```
Cys Glu Asn Lys Ile Ile Ser Phe Lys Glu Met Asn Pro Pro
 1               5                   10
```

<210> SEQ ID NO 47
<211> LENGTH: 14
<212> TYPE: PRT
<213> ORGANISM: Homo sapiens

<400> SEQUENCE: 47

```
Ile Ser Phe Lys Glu Met Asn Pro Pro Asp Asn Ile Lys Asp
 1               5                   10
```

<210> SEQ ID NO 48
<211> LENGTH: 14
<212> TYPE: PRT
<213> ORGANISM: Homo sapiens

<400> SEQUENCE: 48

```
Met Asn Pro Pro Asp Asn Ile Lys Asp Thr Lys Ser Asp Ile
 1               5                   10
```

<210> SEQ ID NO 49
<211> LENGTH: 14
<212> TYPE: PRT
<213> ORGANISM: Homo sapiens

<400> SEQUENCE: 49

```
Asn Ile Lys Asp Thr Lys Ser Asp Ile Ile Phe Phe Gln Arg
 1               5                   10
```

<210> SEQ ID NO 50
<211> LENGTH: 14
<212> TYPE: PRT
<213> ORGANISM: Homo sapiens

<400> SEQUENCE: 50

```
Lys Ser Asp Ile Ile Phe Phe Gln Arg Ser Val Pro Gly His
 1               5                   10
```

<210> SEQ ID NO 51
<211> LENGTH: 14
<212> TYPE: PRT
<213> ORGANISM: Homo sapiens

<400> SEQUENCE: 51

```
Phe Phe Gln Arg Ser Val Pro Gly His Asp Asn Lys Met Gln
 1               5                   10
```

<210> SEQ ID NO 52
<211> LENGTH: 14
<212> TYPE: PRT
<213> ORGANISM: Homo sapiens

<400> SEQUENCE: 52

Val Pro Gly His Asp Asn Lys Met Gln Phe Glu Ser Ser Ser

<210> SEQ ID NO 53
<211> LENGTH: 14
<212> TYPE: PRT
<213> ORGANISM: Homo sapiens

<400> SEQUENCE: 53

Asn Lys Met Gln Phe Glu Ser Ser Ser Tyr Glu Gly Tyr Phe
1               5                   10

<210> SEQ ID NO 54
<211> LENGTH: 14
<212> TYPE: PRT
<213> ORGANISM: Homo sapiens

<400> SEQUENCE: 54

Glu Ser Ser Ser Tyr Glu Gly Tyr Phe Leu Ala Cys Glu Lys
1               5                   10

<210> SEQ ID NO 55
<211> LENGTH: 14
<212> TYPE: PRT
<213> ORGANISM: Homo sapiens

<400> SEQUENCE: 55

Glu Gly Tyr Phe Leu Ala Cys Glu Lys Glu Arg Asp Leu Phe
1               5                   10

<210> SEQ ID NO 56
<211> LENGTH: 14
<212> TYPE: PRT
<213> ORGANISM: Homo sapiens

<400> SEQUENCE: 56

Ala Cys Glu Lys Glu Arg Asp Leu Phe Lys Leu Ile Leu Lys
1               5                   10

<210> SEQ ID NO 57
<211> LENGTH: 14
<212> TYPE: PRT
<213> ORGANISM: Homo sapiens

<400> SEQUENCE: 57

Arg Asp Leu Phe Lys Leu Ile Leu Lys Lys Glu Asp Glu Leu
1               5                   10

<210> SEQ ID NO 58
<211> LENGTH: 14
<212> TYPE: PRT
<213> ORGANISM: Homo sapiens

<400> SEQUENCE: 58

Leu Ile Leu Lys Lys Glu Asp Glu Leu Gly Asp Arg Ser Ile
1               5                   10

<210> SEQ ID NO 59
<211> LENGTH: 14
<212> TYPE: PRT
<213> ORGANISM: Homo sapiens

<400> SEQUENCE: 59

Glu Asp Glu Leu Gly Asp Arg Ser Ile Met Phe Thr Val Gln
1               5                   10

<210> SEQ ID NO 60
<211> LENGTH: 12
<212> TYPE: PRT
<213> ORGANISM: Homo sapiens

<400> SEQUENCE: 60

Asp Arg Ser Ile Met Phe Thr Val Gln Asn Glu Asp
1               5                   10

<210> SEQ ID NO 61
<211> LENGTH: 157
<212> TYPE: PRT
<213> ORGANISM: Homo sapiens

<400> SEQUENCE: 61

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 62
<211> LENGTH: 341
<212> TYPE: DNA
<213> ORGANISM: Homo sapiens
<220> FEATURE:
<221> NAME/KEY: CDS
<222> LOCATION: (1)..(339)

<400> SEQUENCE: 62 cag gtc cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15 tcg atg aaa gtc tcc tgt aag act tct gga tac acc ttc acc ggc tat       96
Ser Met Lys Val Ser Cys Lys Thr Ser Gly Tyr Thr Phe Thr Gly Tyr
                20                  25                  30 tat atc cac tgg gtg cga cag gcc cct gga cag gga ttc gag tgg ata      144
Tyr Ile His Trp Val Arg Gln Ala Pro Gly Gln Gly Phe Glu Trp Ile
            35                  40                  45 gga cgg ctc aac ccc acc act ggt gac gca aat ttt gca gaa aag ttt      192
Gly Arg Leu Asn Pro Thr Thr Gly Asp Ala Asn Phe Ala Glu Lys Phe
        50                  55                  60 cag ggc agg gtc gcc ctg acc aga gac acg tcc atc agc aca gcc tat      240
Gln Gly Arg Val Ala Leu Thr Arg Asp Thr Ser Ile Ser Thr Ala Tyr
65                  70                  75                  80

```
tta caa cta gac agc ctc aaa tct gac gac acg gcc gta tat tat tgt    288
Leu Gln Leu Asp Ser Leu Lys Ser Asp Asp Thr Ala Val Tyr Tyr Cys
                85                  90                  95 gcg gga aaa gag ggt gcc tgg ggc cag ggc acc ctg gtc acc gtc tcg    336
Ala Gly Lys Glu Gly Ala Trp Gly Gln Gly Thr Leu Val Thr Val Ser
            100                 105                 110 agt gg                                                              341
Ser

<210> SEQ ID NO 63
<211> LENGTH: 113
<212> TYPE: PRT
<213> ORGANISM: Homo sapiens

<400> SEQUENCE: 63

Gln Val Gln Leu Val Gln Ser Gly Ala Glu Val Lys Lys Pro Gly Ala
 1               5                  10                  15

Ser Met Lys Val Ser Cys Lys Thr Ser Gly Tyr Thr Phe Thr Gly Tyr
                20                  25                  30

Tyr Ile His Trp Val Arg Gln Ala Pro Gly Gln Gly Phe Glu Trp Ile
            35                  40                  45

Gly Arg Leu Asn Pro Thr Thr Gly Asp Ala Asn Phe Ala Glu Lys Phe
        50                  55                  60

Gln Gly Arg Val Ala Leu Thr Arg Asp Thr Ser Ile Ser Thr Ala Tyr
65                  70                  75                  80

Leu Gln Leu Asp Ser Leu Lys Ser Asp Asp Thr Ala Val Tyr Tyr Cys
                85                  90                  95

Ala Gly Lys Glu Gly Ala Trp Gly Gln Gly Thr Leu Val Thr Val Ser
            100                 105                 110

Ser

<210> SEQ ID NO 64
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 64 tct tct gag ctg act cag gac cct gct gtg tct gtg gcc ttg gga cag     48
Ser Ser Glu Leu Thr Gln Asp Pro Ala Val Ser Val Ala Leu Gly Gln
 1               5                  10                  15 aca gtc agg atc aca tgc caa gga gac agc ctc aga cac ttt tat cca     96
Thr Val Arg Ile Thr Cys Gln Gly Asp Ser Leu Arg His Phe Tyr Pro
                20                  25                  30 aac tgg tac cag cag aag cca gga cag gcc cct gta ctt gtc atc tat    144
Asn Trp Tyr Gln Gln Lys Pro Gly Gln Ala Pro Val Leu Val Ile Tyr
            35                  40                  45 ggt aaa aac aat cgg ccc tca ggg atc cca gac cga ttc tct ggc tcc    192
Gly Lys Asn Asn Arg Pro Ser Gly Ile Pro Asp Arg Phe Ser Gly Ser
        50                  55                  60 ggc tca gga aac aca ggt tcc ttg acc atc act ggg gcc cag gcg gaa    240
Gly Ser Gly Asn Thr Gly Ser Leu Thr Ile Thr Gly Ala Gln Ala Glu
65                  70                  75                  80 gat gag gct gac tat tac tgt ggc tcc cgg gac agc agt ggt atc cat    288
Asp Glu Ala Asp Tyr Tyr Cys Gly Ser Arg Asp Ser Ser Gly Ile His
                85                  90                  95 gtg gta ttc ggc gga ggg acc aag gtc acc gtc cta ggt                327
```

```
Val Val Phe Gly Gly Gly Thr Lys Val Thr Val Leu Gly
            100                 105
```

<210> SEQ ID NO 65
<211> LENGTH: 109
<212> TYPE: PRT
<213> ORGANISM: Homo sapiens

<400> SEQUENCE: 65

```
Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg His Phe Tyr Pro
             20                  25                  30

Asn Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60

Gly Ser Gly Asn Thr Gly Ser Leu Thr Ile Thr Gly Ala Gln Ala Glu
 65                  70                  75                  80

Asp Glu Ala Asp Tyr Tyr Cys Gly Ser Arg Asp Ser Ser Gly Ile His
                 85                  90                  95

Val Val Phe Gly Gly Gly Thr Lys Val Thr Val Leu Gly
            100                 105
```

<210> SEQ ID NO 66
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 66

```
gag gtg cag ctg ttg gag tct ggg gga ggc ttg gta cag cct ggg ggg     48
Glu Val Gln Leu Leu Glu Ser Gly Gly Gly Leu Val Gln Pro Gly Gly
  1               5                  10                  15 tcc ctg aga ctc tcc tgt gca gcc tct gga ttc acc ttt agc agc tat     96
Ser Leu Arg Leu Ser Cys Ala Ala Ser Gly Phe Thr Phe Ser Ser Tyr
             20                  25                  30 gcc atg agc tgg gtc cgc cag gct cca ggg aag ggg ctg gag tgg gtc    144
Ala Met Ser Trp Val Arg Gln Ala Pro Gly Lys Gly Leu Glu Trp Val
         35                  40                  45 tca gct att agt ggt agt ggt ggt agc aca tac tac gca gac tcc gtg    192
Ser Ala Ile Ser Gly Ser Gly Gly Ser Thr Tyr Tyr Ala Asp Ser Val
     50                  55                  60 aag ggc cgg ttc acc atc tcc aga gac aat tcc aag aac acg ctg tat    240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gcc gtg tat tac tgt    288
Leu Gln Met Asn Ser Leu Arg Ala Glu Asp Thr Ala Val Tyr Tyr Cys
                 85                  90                  95 gcg aga gat gac gat gac tac gac ttt gac tac tgg ggc cgg ggg aca    336
Ala Arg Asp Asp Asp Asp Tyr Asp Phe Asp Tyr Trp Gly Arg Gly Thr
            100                 105                 110 atg gtc acc gtc tcg agt                                             354
Met Val Thr Val Ser Ser
            115
```

<210> SEQ ID NO 67
<211> LENGTH: 118
<212> TYPE: PRT

<213> ORGANISM: Homo sapiens

<400> SEQUENCE: 67

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Asp Asp Tyr Asp Phe Asp Tyr Trp Gly Arg Gly Thr
            100                 105                 110

Met Val Thr Val Ser Ser
        115
```

<210> SEQ ID NO 68
<211> LENGTH: 334
<212> TYPE: DNA
<213> ORGANISM: Homo sapiens
<220> FEATURE:
<221> NAME/KEY: CDS
<222> LOCATION: (1)..(333)

<400> SEQUENCE: 68

```
cag tct gtg ttg acg cag ccg ccc tca gcg tct ggg gcc ccc ggt cag    48
Gln Ser Val Leu Thr Gln Pro Pro Ser Ala Ser Gly Ala Pro Gly Gln
 1               5                  10                  15 agg gtc acc atc tct tgt tct gga agc agc tcc aac atc gga att aat    96
Arg Val Thr Ile Ser Cys Ser Gly Ser Ser Ser Asn Ile Gly Ile Asn
            20                  25                  30 gct gta aac tgg tac cag cag ctc cca gga acg gcc ccc aaa ctc ctc   144
Ala Val Asn Trp Tyr Gln Gln Leu Pro Gly Thr Ala Pro Lys Leu Leu
        35                  40                  45 atc tat ggt aat gat cag cgg ccc tca ggg gtc cct gac cga ttc tct   192
Ile Tyr Gly Asn Asp Gln Arg Pro Ser Gly Val Pro Asp Arg Phe Ser
    50                  55                  60 ggc tcc aag tct ggc acc tca gcc tcc ctg gcc atc agt ggg ctc cag   240
Gly Ser Lys Ser Gly Thr Ser Ala Ser Leu Ala Ile Ser Gly Leu Gln
65                  70                  75                  80 tct gag gat gag gct gat tat aac tgt gca gca tgg gat gac agc ctg   288
Ser Glu Asp Glu Ala Asp Tyr Asn Cys Ala Ala Trp Asp Asp Ser Leu
                85                  90                  95 agt ggt ccg gtg ttc ggc gga ggg acc aag ctg acc gtc cta ggt g     334
Ser Gly Pro Val Phe Gly Gly Gly Thr Lys Leu Thr Val Leu Gly
            100                 105                 110
```

<210> SEQ ID NO 69
<211> LENGTH: 111
<212> TYPE: PRT
<213> ORGANISM: Homo sapiens

<400> SEQUENCE: 69

```
Gln Ser Val Leu Thr Gln Pro Pro Ser Ala Ser Gly Ala Pro Gly Gln
 1               5                  10                  15

Arg Val Thr Ile Ser Cys Ser Gly Ser Ser Ser Asn Ile Gly Ile Asn
```

-continued

```
                20                  25                  30
Ala Val Asn Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Asn Cys Ala Ala Trp Asp Asp Ser Leu
                85                  90                  95

Ser Gly Pro Val Phe Gly Gly Gly Thr Lys Leu Thr Val Leu Gly
                100                 105                 110

<210> SEQ ID NO 70
<211> LENGTH: 66
<212> TYPE: PRT
<213> ORGANISM: Homo sapiens

<400> SEQUENCE: 70

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val
65

<210> SEQ ID NO 71
<211> LENGTH: 34
<212> TYPE: PRT
<213> ORGANISM: Homo sapiens

<400> SEQUENCE: 71

Phe Leu Ala Cys Glu Lys Glu Arg Asp Leu Phe Lys Leu Ile Leu Lys
1               5                   10                  15

Lys Glu Asp Glu Leu Gly Asp Arg Ser Ile Met Phe Thr Val Gln Asn
                20                  25                  30

Glu Asp
```

ANTIBODIES THAT BIND IL-18 AND METHODS OF INHIBITING IL-18 ACTIVITY

RELATED APPLICATIONS

This application is a non-provisional application claiming priority to U.S. provisional application Ser. No. 60/181,608, filed Feb. 10, 2000, entitled, "Antibodies that Bind Human Interleukin-18 and Methods of Making and Using" the contents of which are hereby incorporated by reference. In addition, the contents of all cited references, including literature references, issued patents, and published patent applications, as cited throughout this application are hereby expressly incorporated by reference.

BACKGROUND OF THE INVENTION

Interleukin-18 (IL-18) was originally described in 1989 as interferon-gamma inducing factor (IGIF) and is a pro-inflammatory cytokine with various functions in addition to an ability to induce interferon gamma. These biological properties include activation of NF-κb, Fas ligand expression, the induction of both CC and CXC chemokines, and increased production of competent human immunodeficiency virus.

Due to the ability of IL-18 to induce interferon gamma production in T cells and macrophages, it plays an important role in Th1-type immune responses and participates in both innate and acquired immunity. IL-18 is related to the IL-1 family in terms of both structure and function. For reviews of IL-18 structure, function and biological activity, see for example Dinarello, C. et al. (1998) *J. Leukoc. Biol.* 63:658-654; Dinarello, C. A. (1999) *Methods* 19:121-132; and Dinarello, C. A. (1999) *J. Allergy Clin. Immunol.* 103:11-24.

It would be desirable to use to modulate IL-18 in a variety of human immune responses. In particular, antibodies that bind to and neutralize IL-18 are particularly desirable. Moreover, murine IL-18 antibodies are limited for their use in vivo due to problems associated with administration of mouse antibodies to humans, such as short serum half life, an inability to trigger certain human effector functions and elicitation of an unwanted immune response against the mouse antibody in a human (the "human anti-mouse antibody" (HAMA) reaction).

In general, attempts to overcome the problems associated with use of fully-murine antibodies in humans, have involved genetically engineering the antibodies to be more "human-like." For example, chimeric antibodies, in which the variable regions of the antibody chains are murine-derived and the constant regions of the antibody chains are human-derived, have been prepared (Junghans, et al. (1990) *Cancer Res.* 50:1495-1502; Brown et al. (1991) *Proc. Natl. Acad. Sci.* 88:2663-2667; Kettleborough et al. (1991) *Protein Engineering* 4:773-783). However, because these chimeric and humanized antibodies still retain some murine sequences, they still may elicit an unwanted immune reaction, the human anti-chimeric antibody (HAMA) reaction, especially when administered for prolonged periods.

A preferred IL-18 inhibitory agent to murine antibodies or derivatives thereof (e.g., chimeric or humanized antibodies) would be an entirely human anti-IL-18 antibody, since such an agent should not elicit the HAMA reaction, even if used for prolonged periods. However, such antibodies have not been described in the art and, therefore are still needed.

SUMMARY OF THE INVENTION

This invention pertains to compounds, such as antibodies, that bind human IL-18, as well as methods of making and using such compounds or antibodies.

In one aspect, the invention pertains to a compound capable of binding a human IL-18 amino acid sequence, or portion thereof, where the amino acid comprises an N- or C-terminal portion of human IL-18 such as provided in SEQ ID NO: 70 or SEQ ID NO: 71. In one embodiment, the compound is a small molecule, peptide, polypeptide, antibody, or antibody fragment, such as a fully human antibody or fragment.

In another aspect, the invention pertains to a human monoclonal antibody, or antigen-binding portion thereof, capable of binding to human IL-18. In other embodiments, the antibody or fragment thereof, dissociates from human IL-18, as determined by plasmon resonance, with a koff rate constant of 0.1 s-1 or less, 1×10E-2 s-1 or less, 1×10E-3 s-1 or less, 1×10E-4 s-1 or less, 1×10E-5 s-1 or less, 1×10E-6 s-1 or less, or inhibits human IL-18 activity with an IC50 of 1×10E-6 or less, 1×10E-7 or less, 1×10E-8 or less, 1×10E-9, 1×10E-10 or less, or 1×10E-11 or less.

In another aspect, the invention pertains to an isolated antibody, or an antigen-binding portion thereof, that binds an epitope of human IL-18 comprising amino acids PLFED-MTDSDCRDNA (SEQ ID NO: 1), VIRNLNDQVLFIDQ (SEQ ID NO: 33), or a portion of either. Preferably, the antibody is a neutralizing antibody. Preferably, the antibody is a human antibody. In various embodiments, the antibody is a recombinant antibody (e.g., a single-chain antibody (scFv)), or a monoclonal antibody.

In other embodiments, the isolated antibody, or antigen-binding portion thereof, binds to an epitope of human IL-18, or a portion of either, where the antibody, or antigen-binding portion thereof, dissociates from human IL-18 with a $k_{off}$ rate constant of $0.1 \text{ s}^{-1}$ or less, as determined by surface plasmon resonance, or which inhibits human IL-18 activity with an $IC_{50}$ of $1\times10^{-6}$M or less. Alternatively, the antibody, or an antigen-binding portion thereof, may dissociate from human IL-18 with a $k_{off}$ rate constant of $1\times10^{-2} \text{ s}^{-1}$ or less, as determined by surface plasmon resonance, or may inhibit human IL-18 activity with an $IC_{50}$ of $1\times10^{-7}$M or less. Alternatively, the antibody, or an antigen-binding portion thereof, may dissociate from human IL-18 with a $k_{off}$ rate constant of $1\times10^{-3} \text{ s}^{-1}$ or less, as determined by surface plasmon resonance, or may inhibit human IL-18 activity with an $IC_{50}$ of $1\times10^{-8}$M or less. Alternatively, the antibody, or an antigen-binding portion thereof, may dissociate from human IL-18 with a $k_{off}$ rate constant of $1\times10^{-4} \text{ s}^{-1}$ or less, as determined by surface plasmon resonance, or may inhibit human IL-18 activity with an $IC_{50}$ of $1\times10^{-9}$M or less. Alternatively, the antibody, or an antigen-binding portion thereof, may dissociate from human IL-18 with a $k_{off}$ rate constant of $1\times10^{-5} \text{ s}^{-1}$ or less, as determined by surface plasmon resonance, or may inhibit human IL-18 activity with an $IC_{50}$ of $1\times10^{-10}$M or less. Alternatively, the antibody, or an antigen-binding portion thereof, may dissociate from human IL-18 with a $k_{off}$ rate constant of $1\times10^{-6} \text{ s}^{-1}$ or less, as determined by surface plasmon resonance, or may inhibit human IL-18 activity with an $IC_{50}$ of $1\times10^{-11}$M or less.

Another aspect of the invention pertains to an isolated human antibody, or an antigen-binding portion thereof, containing at least one variable region CDR domain capable of binding an epitope of human IL-18. In related embodiments, the isolated antibody, or an antigen-binding portion thereof, has a variable region containing a heavy and/or light chain CDR1 domain, CDR2 domain, or CDR3 domain as set forth in Table 6 or 9 which can have, e.g., one or more amino acid substitutions or insertions at or adjacent to any of the Kabat positions indicated in Tables 7-8 and 10-11. In a preferred embodiment, the isolated antibody, or an antigen-binding portion thereof, contains a light chain variable region (LCVR) containing the amino acid sequence of SEQ ID NO: 29 and a heavy chain variable region (HCVR) containing the amino acid sequence of SEQ ID NO: 26. In another preferred embodiment, the isolated antibody, or an antigen-binding portion thereof, contains a light chain variable region (LCVR) having the amino acid sequence of SEQ ID NO: 29 and a heavy chain variable region (HCVR) having the amino acid sequence of SEQ ID NO: 27.

Another aspect of the invention pertains to pharmaceutical compositions comprising an antibody, or antigen-binding portion thereof, of the invention and a pharmaceutically acceptable carrier. In one embodiment, the pharmaceutical composition further comprises at least one additional therapeutic agent for treating a disorder in which IL-18 activity is detrimental.

Another aspect of the invention pertains to methods of making an antibody that binds human interleukin-18 (IL-18). The invention provides a method comprising exposing an antibody repertoire to an antigen comprising an epitope of human IL-18 comprising amino acids PLFEDMTDSD-CRDNA (SEQ ID NO: 1)), VIRNLNDQVLFIDQ (SEQ ID NO: 33), or a portion of either; and selecting from the antibody repertoire an antibody that binds the epitope of human IL-18 comprising amino acids PLFEDMTDSDCRDNA (SEQ ID NO: 1), VIRNLNDQVLFIDQ (SEQ ID NO: 33), or a portion of either.

In one embodiment, the antibody repertoire is an in vivo repertoire in an animal and the method comprises immunizing the animal with the antigen comprising the epitope of human IL-18 comprising amino acids PLFEDMTDSD-CRDNA (SEQ ID NO: 1), VIRNLNDQVLFIDQ (SEQ ID NO: 33), the N- or C-terminal portion of human IL-18 (SEQ ID NOS: 70-71), or a portion of any of these epitopes. In another embodiment, the antibody repertoire is a recombinant antibody library and the method comprises screening the library with an antigen containing the epitope of human IL-18 having the amino acids PLFEDMTDSDCRDNA (SEQ ID NO: 1), VIRNLNDQVLFIDQ (SEQ ID NO: 33), peptides represented by SEQ ID NOS: 31-32 and 34-60, or a portion of any of the foregoing. Preferably, the library is a human antibody library.

In another aspect, the invention provides an isolated nucleic acid encoding an antibody of any of the above aspects, e.g., a heavy and/or light chain variable region, or portion thereof. In related embodiments, the isolated nucleic acid encoding the anti-IL-18 antibody, or portion thereof, is in a recombinant expression vector, e.g., for expression in a host cell.

Thus, in another aspect, the invention pertains to a method of using the foregoing host cell into which the recombinant expression vector has been introduced, for synthesizing an antibody that binds human IL-18, by culturing the host cell in a culture medium until an antibody that binds human IL-18 is synthesized by the cell.

Another aspect of the invention pertains to a method for inhibiting human IL-18 activity comprising contacting human IL-18 with the antibody, or antigen-binding portion thereof, of the invention such that human IL-18 activity is inhibited.

Yet another aspect of the invention pertains to a method for inhibiting human IL-18 activity in a human subject suffering from a disorder in which IL-18 activity is detrimental, comprising administering to the human subject the antibody, or antigen-binding portion thereof, of the invention such that human IL-18 activity in the human subject is inhibited. In one embodiment, the anti-IL-18 antibody may be administered, e.g., before, concurrent, or after, an additional agent such as an anti-IL-12 antibody or antigen binding fragment thereof, methotrexate, anti-TNF antibody or antigen binding fragment thereof, corticosteroids, cyclosporin, rapamycin, FK506, or a non-steroidal anti-inflammatory agent.

DETAILED DESCRIPTION OF THE INVENTION

Figure 1:
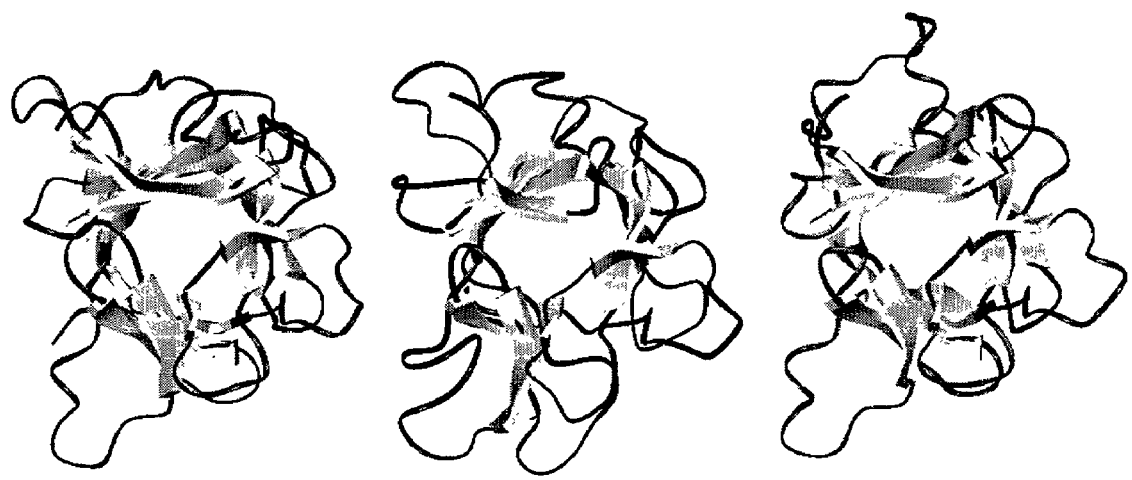
FIG. 1 shows the structural model of IL-18 (center) as compared to IL-1β (left) and IL1RA (right).

This invention pertains to the selection of peptide epitopes that are capable of generating neutralizing antibodies to IL-18 mediated signal transduction, the preparation of antibodies to these epitopes and the use of such antibodies, including use to treat disorders involving IL-18. The strategy of selecting epitopes entails construction of an homology model of the IL-18 protein and its corresponding receptor. A combination of visual inspection and computational evaluation is then used to select representative peptide segments for synthesis and antibody generation. Amino acid sequences shown herein use the standard one-letter abbreviation code.

Selection of IL-18 Epitopes

The program Modeler (Sali, A. et al., *Evaluation of comparative protein modeling by MODELLER*. Proteins: Struct., Funct., Genet. (1995), 23(3), pp. 318-26. CODEN: PSFGEY; ISSN: 0887-3585) was used to generate homology models for both IL-18 and the IL-18 receptor. The X-ray crystal structures of IL-1β (Priestle, J., et al. *The three-dimensional structure of human interleukin-1.beta. refined to 2.0.ANG. resolution.* Prog. Clin. Biol. Res. (1990), 349 (Cytokines Lipocortins Inflammation Differ.), pp. 297-307) and IL-1RA (Schreuder, H. et al., *Refined crystal structure of the interleukin-1 receptor antagonist: presence of a disulfide link and a cis-proline.* Eur. J. Biochem. (1995), 227(3), pp. 838-47) are available and were used as reference coordinates for the model construction of IL-18. The IL-1 receptor structure (Vigers, G., et al. *Crystal structure of the type-I interleukin-*

1-*receptor complexed with interleukin*-1.*beta*. Nature (London) (1997), 386(6621), pp. 190-194) was used to model the IL-18 receptor.

The structural model building for IL-18 and the IL-18 receptor is described further below.

IL-18 Model Building

The overall sequence homology with these two proteins (i.e., IL-1β and IL-18) is low, however, there is compelling evidence that IL-18 is a member of the IL-1 family (see Dinarello, C. A. *IL-18: a TH1-inducing, proinflammatory cytokine and new member of the IL-1 family*. J. Allergy Clin. Immunol. (1999), 103(1, Pt. 1), pp. 11-24) and that the overall protein fold is very similar. Like IL-113, IL-18 is initially secreted in a pro form. Both pro-IL-1 β and pro-IL-18 are activated by IL-1 β-converting enzyme (ICE) (Fantuzzi, G. and Dinarello, C. A. *Interleukin*-18 *and interleukin*-1β: *two cytokine substrates for ICE* (*caspase*-1). J. Clin. Immunol. (1999), 19(1), pp. 1-11). It is also known that the IL-1 receptor and the IL-18 receptor are similar (Dinarello, C. A. et al. *Overview of interleukin-18: more than an interferon-γ inducing factor*. J. Leukocyte Biol. (1998), 63(6), 658-664). IL-1β is capable of binding to the IL-18 receptor. As a final argument, IL-1 β and IL-1RA display an identical fold, even though the overall sequence homology between these two proteins is on a par with the sequence homology with IL-18. The sequence alignment between the three proteins (i.e., IL-18, IL-1β and IL1-RA) was constructed manually with the program InsightII. This alignment can be seen in Table 1:

The resulting IL-18 structure is pictured in FIG. 1 along with IL-1β and IL-1RA. The overall quality as assessed by the program What_Check (Hooft, R. W. et al., *Errors in Protein Structures*. Nature (1996) 381, pp. 272) is reasonable, but a bit low (see Table 3 below).

TABLE 3

Structural Z-scores from What_Check (Positive is better than average)

|  | IL-1β | IL-1RA | IL-1 Rec | IL-18 (model) | IL-18 Rec (model) |
|---|---|---|---|---|---|
| Packing Quality | −1.6 | −2.3 | −3.6 | −5.5 | −5.7 |
| Ramachandran Plot | −2.0 | −1.3 | −2.9 | −3.3 | −2.3 |
| Rotamer Normality | −1.6 | −0.8 | −1.5 | −0.6 | −0.6 |
| Backbone Conformation | −1.7 | +0.5 | −1.6 | −5.6 | −2.7 |

TABLE 1

Sequence alignment for IL-18 relative to IL-1β and IL-1RA

```
                24
IL-18:     YFGK-LESKLS-VIRNLNDQVLFIDQGNRPLFE--DMT-DSDCRD--NAP
IL-1β:       AP-VRS-LNCTLRDSQQKSLVMS-G--P-YELKALHLQGQ--D--MEQ
IL-1RA:      SSKMQA-FR--IWDVNQKTFYLR-N--N--QLVAGYLQGP--NVNLEE

80
IL-18:     RTIFIISMY-KDSQPRG-MAVTISVKCEKISTLSC----ENK-IISFKEM
IL-1β:     QVVFSMS-FVQGEESNDKIPVALGLK-EKNLYLSCVLK-DDKPTLQLESV
IL-1RA:    KI--DV---VP-IEPH---ALFLGIH-GGKMCLSCV-KSGDETRLQLEAV

123
IL-18:     NPPDNI-KDTKSDIIF-FQRSVPGHDNKMQFESSSYEGYFLACE-KERDL
IL-1β:     DPKNYP-KK-KMEKRFVFNK-I-EINNKLEFESAQFPNWYISTS-QAENM
IL-1RA:    NITDLSENR-KQDKRFAFIR-S-DSGPTTSFESAACPGWFLCTAMEADQ-

170
IL-18:     FKLILKKED-ELGDRSIM-FTVQNED          (SEQ ID NO: 4)
IL-1β:     -PVFL--GG-TKGGQDITDFTMQFVSS         (SEQ ID NO: 5)
IL-12RA:   -PVSL--TNMPDEGVMVTKFYFQED           (SEQ ID NO: 6)
```

The sequence homology between these sequences is listed in Table 2. The upper triangle is percent strict sequence identity and the lower triangle is percent conservative sequence homology. Only the portions of the total sequences reported in Table 1 are considered in Table 2. As was mentioned above, the overall homology is low but consistent across the family.

TABLE 2

Sequence homology between IL-1 family members

| Molecule | IL-18 | IL-1β | IL-1RA | IL-1 Rec | IL-18 Rec |
|---|---|---|---|---|---|
| IL-18 | — | 20.0 | 21.8 | — | — |
| IL-1b | 53.5 | — | 27.5 | — | — |
| IL-1RA | 50.6 | 54.4 | — | — | — |
| IL-1 Rec | — | — | — | — | 26.1 |
| IL-18 Rec | — | — | — | 50.5 | — |

However, the assessment of the reference structures by What_Check is also low, suggesting that this protein fold is poorly represented in the database of reference structures. Undoubtedly though, the low sequence homology contributed to a less than perfect final structure in spite of our confidence in the overall protein fold. However, for the purpose of choosing epitopes for antibody generation, this structure is considered to be sufficient.

IL-18 Receptor Model Building

The structure of the IL-18 receptor was also generated using the program Modeler. The reference coordinates were from the IL-1 receptor. As in the case of the cytokines associated with these receptors, the overall sequence identity is low, but sufficient to generate an alignment. The sequence homology figures are included in Table 2 above. The alignment was generated manually using the program InsightII and is presented in Table 4.

TABLE 4

Sequence alignment for the IL-18 receptor relative to the IL-I Receptor

```
               22
IL-18 Rec:     CTSRPHITVVEGEPFYLKHCSCSLAHEIETTTKSWYKSSGSQEHVELNPR
IL-1 Rec  :    CKEREEKIILVSSANEIDVRPCPLNPNEHKGTITWYKDD-SKTPVSTEQA
               72
IL-18 Rec:     SSSRIALHDCVLEFWPVELNDTGSYFFQMKNYTQKWKLNVIRRNKHS---
IL-1 Rec  :    S--RIHQHKEKLWFVPAKVEDSGHYYCVVRNSSYCLRIKISAKFVENEPN
               119
IL-18 Rec:     -CFTERQVTSKIVEVKKFFQITCENSYYQTLVNST----SLYKNCKKLLL
IL-1 Rec  :    LCYNAQAIFKQKLPVAGDGGLVCPYMEFFKNENNELPKLQWYKDCKPLLL
               163
IL-18 Rec:     EN-----NKNPTIKKNAEFEDQGYYSCVHFLHHNGKLFNITKTFNITIVE
IL-1 Rec  :    DNIHFSGVKDRLIVMNVAEKHRGNYTCHASYTYLGKQYPITRVIEFITLE
               209
IL-18 Rec:     DRSNIVPVLLGPKLNHVAVELGKNVRLNCSALLNEEDVIYWMF-GEE-NG
IL-1 Rec  :    ENKPTRPVIVSPANETMEVDLGSQIQLICNVTGQLSDIAYWKWNGSVIDE
               257
IL-18 Rec:     SDPNIHEE-KEMRIMTPEGKWHASKVLRIENIGESNLNVLYNCTVASTGG
IL-1 Rec  :    DDPVLGEDYYSVENPANKRRSTLITVLNISEIESRFYKHPFTCFAKNTHG
               306
IL-18 Rec:     TDTKSFILVRKAD (SEQ ID NO: 7)
IL-1 Rec  :    IDAAYIQLIYPVT (SEQ ID NO: 8)
```

Figure 3:
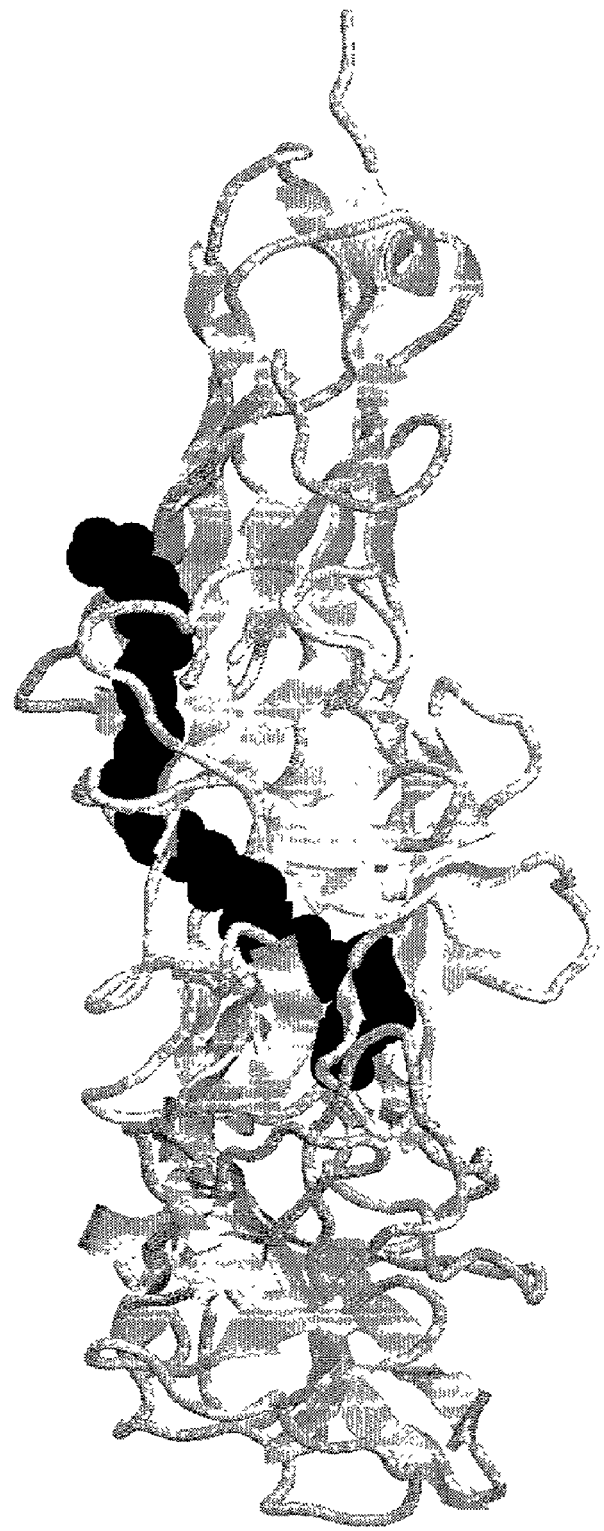
FIG. 3 shows a structural model of IL-18 complexed with the IL-18 receptor, wherein the peptide epitope comprising amino acids YFGKLESKLSVIRN (SEQ ID NO: 33) of IL-18 is indicated in dark gray. This peptide epitope is bound by the anti-IL-18 antibody LT28.
Figure 4:
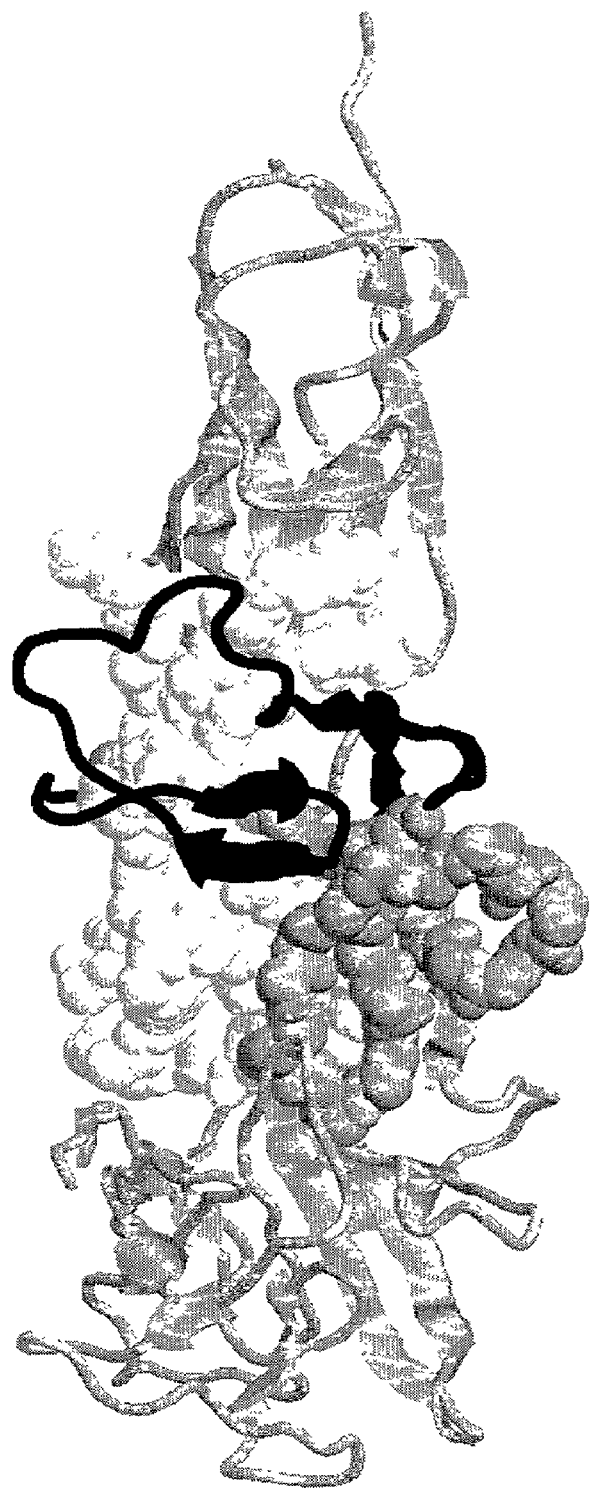
FIG. 4 shows a structural model of full length IL-18 complexed with the IL-18 receptor. The spherical light and dark gray epitopes represent the N and C terminal contact epitopes of IL-18 (respectively, SEQ ID NOS: 70 and 71).

The overall quality of the structure of the IL-18 receptor as determined using the Modeler program is reasonable but again scores somewhat low according to What_Check (see Table 3 above). The confidence that can be placed on the overall fold comes primarily from the fact that IL-1β binds to both the IL-1 and IL-18 receptor. The low sequence homology certainly contributes to the quality of the final structure, however, as in the case of the associated cytokines above, this current structure is considered to be sufficient. As an additional exercise, the IL-18 peptide epitope bound by LT28 (SEQ ID NO: 33) was modeled when complexed with the IL-18 receptor (FIG. 3). As a final exercise, a model of the IL-18/IL-18 receptor complex was generated based on the IL-1β/IL-1 receptor structure (FIG. 4). This structure was generated by superimposing the cytokine structures and the receptor structures. No attempt was made to energy minimize the final structure.

Peptide Epitope Selection

The primary purpose of generating structural models was to be able to select suitable peptides based primarily on a visual score. Solvent exposed sections of the proteins and portions of the proteins which were both hydrophilic and buried in the receptor/cytokine complex were considered. A final element considered was based on a selectivity criterion. The selected peptide epitope should be different in sequence from similar portions of other members of the family. Based on this criteria, a peptide from IL-18 was selected. In addition, a comprehensive overlapping panel of peptides (SEQ ID NOS: 31-60) representative of full length human IL-18 (SEQ ID NO: 61) was also made and the sequence of all of these IL-18 related peptides is shown in Table 5, below.

TABLE 5

Selected Peptides Representative of IL-18

| Peptide Sequence | SEQ ID NO: |
| --- | --- |
| PLFEDMTDSDCRDNA | (SEQ ID NO: 1) |
| CPLFEDMTDSDCRDNA | (SEQ ID NO: 2) |
| PLFEDMTDSDCR | (SEQ ID NO: 3) |
| YFGKLESKLSVIRN | (SEQ ID NO: 31) |
| ESKLSVIRNLNDQV | (SEQ ID NO: 32) |

TABLE 5-continued

Selected Peptides Representative of IL-18

| Peptide Sequence | SEQ ID NO: |
| --- | --- |
| VIRNLNDQVLFIDQ (LT28 binding epitope) | (SEQ ID NO: 33) |
| NDQVLFIDQGNRPL | (SEQ ID NO: 34) |
| FIDQGNRPLFEDMT | (SEQ ID NO: 35) |
| NRPLFEDMTDSDCR (2E1 binding epitope) | (SEQ ID NO: 36) |
| EDMTDSDCRDNAPR | (SEQ ID NO: 37) |
| SDCRDNAPRTIFIT | (SEQ ID NO: 38) |
| NAPRTIFITSMYKD | (SEQ ID NO: 39) |
| IFIISMYKDSQPRG | (SEQ ID NO: 40) |
| MYKDSQPRGMAVTI | (SEQ ID NO: 41) |
| QPRGMAVTISVKCE | (SEQ ID NO: 42) |
| AVTISVKCEKISTL | (SEQ ID NO: 43) |
| VKCEKISTLSCENK | (SEQ ID NO: 44) |
| ISTLSCENKIISEK | (SEQ ID NO: 45) |
| CENKIISFKEMNPP | (SEQ ID NO: 46) |
| ISFKEMNPPDNIKD | (SEQ ID NO: 47) |
| MNPPDNIKDTKSDI | (SEQ ID NO: 48) |
| NIKDTKSDIIFFQR | (SEQ ID NO: 49) |
| KSDIIFFQRSVPGH | (SEQ ID NO: 50) |
| FFQRSVPGHDNKMQ | (SEQ ID NO: 51) |
| VPGHDNKMQFESSS | (SEQ ID NO: 52) |
| NKMQFESSSYEGYF | (SEQ ID NO: 53) |
| ESSSYEGYFLACEK | (SEQ ID NO: 54) |
| EGYFLACEKERDLE | (SEQ ID NO: 55) |
| ACEKERDLFKLILK | (SEQ ID NO: 56) |
| RDLFKLILKKEDEL | (SEQ ID NO: 57) |
| LILKKEDELGDRSI | (SEQ ID NO: 58) |
| EDELGDRSIMFTVQ | (SEQ ID NO: 59) |
| DRSIMFTVQNED | (SEQ ID NO: 60) |
| YFGKLESKLSVIRNLNDQVLFIDQGNRPLFEDMTDSDCRDNAPRTIFIISMYKDSQPRGNAVTISVKCEKISTLSCENKIISFKEMNPPDNIKDTKSDIIFFQRSVPGHDNKMQFESSSYEGYFLACEKERDLFKLILKKEDELGDRSIMFTVQNED | LT28 and 2E1 epitopes indicated in bold |

The N-terminal cysteine of the IL-18 peptide represented by SEQ ID NO: 2 is not part of the native IL-18 sequence, but was added as a conjugation site. Accordingly, within the native IL-18 amino acid sequence, the region corresponding to the selected epitope comprises amino acid residues having the amino acid sequence PLFEDMTDSDCRDNA (SEQ ID NO: 1).

Figure 2:
FIG. 2 shows a structural model of IL-18 complexed with the IL-18 receptor, wherein the peptide epitope comprising amino acids PLFEDMTDSDCRDNA (SEQ ID NO: 1) of IL-18 is indicated in dark gray. This peptide epitope is bound by the anti-IL-18 antibody 2E1.

A schematic model of the IL-18 peptide (SEQ ID NO: 1) complexed with the IL-18 receptor is shown in FIG. 2, with this peptide epitope indicated in dark gray.

Subsequent antigenicity calculations were performed on IL-18 peptide sequences, with the result that this peptide scored particularly highly. This peptide was synthesized and used as an epitope to generate antibodies in a rabbit host. Molecular modeling data obtained using the IL-18 peptide PLFEDMTDSDCRDNA (SEQ ID NO: 1) or YFGKLESKLSVIRN (SEQ ID NO: 31) as compared to a cognate receptor, i.e., the IL-18 receptor, as depicted in FIGS. 2 and 3, provides an indication as to what residues a neutralizing antibody or compound may interact with.

An alternative method for peptide epitope selection can be accomplished in the absence of any molecular modeling by screening a panel of representative peptides using immunoselection. In one approach, overlapping peptides representative of the entire protein sequence can be used. In a more limited approach, only certain epitopes are represented in the panel of peptides. In a combined approach, molecular modeling can be used to identify epitopes likely to be important. The identified epitope(s) sequence can then be used to construct a panel of peptides (e.g., overlapping peptides) that are representative of the identified epitope(s). Methods for manufacturing desired peptide sequences can be carried out using standard techniques known in the art.

Once the binding peptide or peptides (e.g., panel of overlapping peptides) has been selected, an immunoscreen for a cognate receptor can be performed. Alternatively, an immunoscreen can be performed with a selected cognate receptor such that a peptide having a certain binding affinity can be identified. Any number of immunoscreens can be employed such that, either a desired receptor or desired peptide can be identified as a candidate binding molecule for further study. Such "bait" and "prey" techniques for analyzing protein-protein interactions, for identifying candidate biding molecules, and/or for scoring binding affinities are described in the art. One preferred technique utilizes phage display as described herein.

Anti-IL-18 Antibodies

The invention provides antibodies, as well as antibody portions thereof, that bind IL-18. Preferably, the antibodies, or portions thereof, are isolated antibodies. Preferably, the antibodies, or portions thereof, are neutralizing antibodies.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or simply "antibody portion"), as used herein, refers to one or more fragments of an antibody that retain the ability to specifically bind to an antigen (e.g., hIL-18). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds hIL-18 is substantially free of antibodies that specifically bind antigens other than hIL-18). An isolated antibody that specifically binds hIL-18 may, however, have cross-reactivity to other antigens, such as IL-18 molecules from other species. Moreover, an isolated antibody may be substantially free of other cellular material and/or chemicals. Further, an isolated antibody, e.g., an isolated human antibody, can be a chimeric antibody wherein, e.g., variable regions, CDR domains, or isotypes derived from a different human source are grafted to the parent human antibody.

A "compound" as used herein, refers to binding molecules such as antibodies, e.g., polyclonal antibodies, monoclonal antibodies, binding fragments thereof (e.g., Fab fragments), single chain antibodies (e.g., scFv), peptides or peptide mimetics, as well as non-peptide based molecules, such as small molecules having ligand binding activity.

A "neutralizing antibody", as used herein (or an "antibody that neutralized hIL-18 activity"), is intended to refer to an antibody whose binding to hIL-18 results in inhibition of the biological activity of hIL-18. This inhibition of the biological activity of hIL-18 can be assessed by measuring one or more indicators of hIL-18 biological activity. These indicators of hIL-18 biological activity can be assessed by one or more of several standard in vitro or in vivo assays known in the art.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

In one aspect, the invention pertains to an isolated antibody, or an antigen-binding portion thereof, that binds an epitope of human IL-18 comprising amino acids PLFEDMTDSDCRDNA (SEQ ID NO: 1) or VIRNLNDQVLFIDQ (SEQ ID NO: 33), or a portion of any of these epitopes. Preferably, the antibody is a neutralizing antibody. Preferably, the antibody is a human antibody. In various embodiments, the antibody is a recombinant antibody or a monoclonal antibody.

In other embodiments, the isolated antibody, or antigen-binding portion thereof, binds to an epitope of human IL-18 comprising amino acids PLFEDMTDSDCRDNA (SEQ ID NO: 1), wherein the antibody, or antigen-binding portion thereof, dissociates from human IL-18 with a $k_{off}$ rate constant of 0.1 s$^{-1}$ or less, as determined by surface plasmon resonance, or which inhibits human IL-18 activity with an IC$_{50}$ of $1\times10^{-6}$M or less. Alternatively, the antibody, or an antigen-binding portion thereof, may dissociate from human IL-18 with a $k_{off}$ rate constant of $1\times10^{-2}$ s$^{-1}$ or less, as determined by surface plasmon resonance, or may inhibit human IL-18 activity with an IC$_{50}$ of $1\times10^{-7}$M or less. Alternatively, the antibody, or an antigen-binding portion thereof, may dissociate from human IL-18 with a $k_{off}$ rate constant of $1\times10^{-3}$ s$^{-1}$ or less, as determined by surface plasmon resonance, or may inhibit human IL-18 activity with an IC$_{50}$ of $1\times10^{-8}$M or less. Alternatively, the antibody, or an antigen-binding portion thereof, may dissociate from human IL-18 with a $k_{off}$ rate constant of $1\times10^{-4}$ s$^{-1}$ or less, as determined by surface plasmon resonance, or may inhibit human IL-18 activity with an IC$_{50}$ of $1\times10^{-9}$M or less. Alternatively, the antibody, or an antigen-binding portion thereof, may dissociate from human IL-18 with a $k_{off}$ rate constant of $1\times10^{-5}$ s$^{-1}$ or less, as determined by surface plasmon resonance, or may inhibit human IL-18 activity with an IC$_{50}$ of $1\times10^{-10}$M or less. Alternatively, the antibody, or an antigen-binding portion thereof, may dissociate from human IL-18 with a $k_{off}$ rate constant of $1\times10^{-6}$ s$^{-1}$ or less, as determined by surface plasmon resonance, or may inhibit human IL-18 activity with an IC$_{50}$ of $1\times10^{-11}$M or less.

Affinity Maturation of Identified Anti-IL-18 Antibodies

The invention also provides for the further modification of an antibody identified as binding to an IL-18 epitope. The modification of the identified anti-IL-18 antibody is to improve binding and/or neutralization activity.

Therapeutic Compositions and Methods for Administering

The invention also provides pharmaceutical compositions comprising an antibody, or antigen-binding portion thereof, of the invention and a pharmaceutically acceptable carrier. In one embodiment, the pharmaceutical composition further comprises at least one additional therapeutic agent for treating a disorder in which IL-18 activity is detrimental.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which IL-18 activity is detrimental. For example, an anti-hIL-18 antibody or antibody portion of the invention may be coformulated and/or coadministered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

Therapeutic Uses

Interleukin 18 plays a critical role in the pathology associated with a variety of diseases involving immune and inflammatory elements. These diseases include, but are not limited to, rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis and vitiligo. The human antibodies, and antibody portions of the invention can be used to treat humans suffering from autoimmune diseases, in particular those associated with inflammation, including, rheumatoid spondylitis, allergy, autoimmune diabetes, autoimmune uveitis, acute liver disease, chronic liver diseases, allergy and asthma, mental disorders (e.g., depression and schizophrenia), and Th2 Type and Th1 Type mediated diseases.

Preferably, the antibodies of the invention or antigen-binding portions thereof, are used to treat rheumatoid arthritis, Crohn's disease, multiple sclerosis, insulin dependent diabetes, mellitus, and psoriasis.

An antibody, or antibody portion, of the invention also can be administered with one or more additional therapeutic agents useful in the treatment of autoimmune and inflammatory diseases.

Antibodies of the invention, or antigen binding portions thereof can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent which imparts a beneficial attribute to the therapeutic composition e.g., an agent which effects the viscosity of the composition.

It should further be understood that the combinations which are to be included within this invention are those combinations useful for their intended purpose. The agents set forth below are illustrative for purposes and not intended to be limited. The combinations which are part of this invention can be the antibodies of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the anti-IL-18 antibodies of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7, (PCT Publication No. WO 97/29131), CA2 (Remicade™), CDP 571, and soluble p55 or p75 TNF receptors, derivatives, thereof, (p75TNFR1gG (Enbrel™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet another preferred combination are other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

The antibodies of the invention, or antigen binding portions thereof, may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, cox-2 inhibitors, cox-2 selective inhibitors (e.g., rofecoxib (VIOXX™; Merck & Co., Inc.)) corticosteroids such as prednisolone, phosphodiesterase inhibitors, adenosine agonists, anti-thrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TNFα converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R) and antiinflammatory cytokines (e.g. IL-4, IL-10, IL-11, IL-13 and TGFβ). Preferred combinations include methotrexate or leflunomide and in moderate or severe rheumatoid arthritis cases, cyclosporine.

Non-limiting examples of therapeutic agents for inflammatory bowel disease with which an antibody, or antibody portion, of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD90 or their ligands. The antibodies of the invention, or antigen binding portions thereof, may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TNFα converting enzyme inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ).

Preferred examples of therapeutic agents for Crohn's disease in which an antibody or an antigen binding portion can be combined include the following: TNF antagonists, for example, anti-TNF antibodies, D2E7 (PCT Publication No. WO 97/29131), CA2 (Remicade), CDP 571, TNFR-Ig constructs, (p75TNFRIgG (Enbrel™) and p55TNFRIgG (Lenercept)) inhibitors and PDE4 inhibitors. Antibodies of the invention or antigen binding portions thereof, can be combined with corticosteroids, for example, budenoside and dexamethasone. Antibodies of the invention or antigen binding portions thereof, may also be combined with agents such as sulfasalazine, 5-aminosalicylic acid and olsalazine, and agents which interfere with synthesis or action of proinflammatory cytokines such as IL-1, for example, IL-1β converting enzyme inhibitors and IL-1ra. Antibodies of the invention or antigen binding portion thereof may also be used with T cell signaling inhibitors, for example, tyrosine kinase inhibitors 6-mercaptopurines. Antibodies of the invention or antigen binding portions thereof, can be combined with IL-11.

Non-limiting examples of therapeutic agents for multiple sclerosis with which an antibody, or antibody portion, of the invention can be combined include the following: corticosteroids; prednisolone; methylprednisolone; azathioprine; cyclophosphamide; cyclosporine; methotrexate; 4-aminopyridine; tizanidine; interferon-β1a (Avonex; Biogen); interferon-β1b (Betaseron; Chiron/Berlex); Copolymer 1 (Cop-1; Copaxone; Teva Pharmaceutical Industries, Inc.); hyperbaric oxygen; intravenous immunoglobulin; clabribine; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80, CD86, CD90 or their ligands. The antibodies of the invention, or antigen binding portions thereof, may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TACE inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which the antibody or antigen binding portion thereof can be combined to include interferon-β, for example, IFNβ1a and IFNβ1b; copaxone, corticosteroids, IL-1 inhibitors, TNF inhibitors, and antibodies to CD40 ligand and CD80.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Methods of Making Anti-IL-18 Antibodies

The anti-IL-18 antibodies of the invention are made using any one of a variety of techniques known in the art for preparing antibodies and using antigens comprising the IL-18 peptide epitope described in subsection I, i.e., an epitope of human IL-18 comprising amino acids PLFEDMTDSDCRDNA (SEQ ID NO: 1).

In general, the methods of the invention for making an antibody that binds human interleukin-18 (IL-18) involve:

exposing an antibody repertoire to an antigen comprising an epitope of human IL-18 comprising amino acids PLFEDMTDSDCRDNA (SEQ ID NO: 1), or portion thereof (e.g., SEQ ID NO: 3 or 33); and selecting from the antibody repertoire an antibody that binds the epitope of human IL-18 comprising amino acids PLFEDMTDSDCRDNA (SEQ ID NO: 1), or portion thereof (e.g., SEQ ID NO: 3 or 33).

In one embodiment, the antibody repertoire is an in vivo repertoire in an animal and the method comprises immunizing the animal with the antigen comprising the epitope of human IL-18 comprising amino acids PLFEDMTDSDCRDNA (SEQ ID NO: 1). In another embodiment, the antibody repertoire is a recombinant antibody library and the method comprising screening the library with the antigen comprising the epitope of human IL-18 comprising amino acids PLFEDMTDSDCRDNA (SEQ ID NO: 1). Preferably, the library is a human antibody library.

Methods for immunizing an animal with an antigen to thereby raise specific antibodies to the antigen are well known in the art. An IL-18 antigen comprising an epitope of human IL-18 comprising amino acids PLFEDMTDSDCRDNA (SEQ ID NO: 1) can be administered to an animal to elicit polyclonal antibodies and specific antibodies that bind the epitope can be isolated by selecting from the polyclonal antibodies those antibodies that bind to the epitope (e.g., by passing the polyclonal antisera over a column that comprises a peptide comprising amino acids PLFEDMTDSDCRDNA (SEQ ID NO: 1) of hIL-18). The antigen used to elicit the polyclonal antibodies can be intact (i.e., full-length) hIL-18 or can be a portion of hIL-18 that includes the epitope of interest, e.g., a synthetic peptide comprising amino acids PLFEDMTDSDCRDNA (SEQ ID NO: 1) of hIL-18. Furthermore, monoclonal antibodies to the epitope can be made from the aforementioned animals using standard hybridoma technology and selection for those hybridomas secreting an antibody that specifically binds the epitope of interest, e.g., by screening the hybridomas with a peptide comprising amino acids PLFEDMTDSDCRDNA (SEQ ID NO: 1) of hIL-18 and selecting for antibodies that bind specifically to the peptide.

In vitro methods also can be used to make the antibodies of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markiand et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, and PCT Publication No. WO 97/29131, the contents of each of which are incorporated herein by reference.

The recombinant antibody library may be from a subject immunized with IL-18, or a portion of IL-18 comprising the epitope of amino acids PLFEDMTDSDCRDNA (SEQ ID NO: 1). Alternatively, the recombinant antibody library may be from a nave subject, i.e., one who has not been immunized with IL-18, such as a human antibody library from a human subject who has not been immunized with human IL-18. Antibodies of the invention are selected by screening the recombinant antibody library with the epitope of amino acids PLFEDMTDSDCRDNA (SEQ ID NO: 1) of human IL-18 to thereby select those antibodies that recognize this epitope. Methods for conducting such screening and selection are well known in the art, such as described in the references in the preceding paragraph.

To select antibodies of the invention having a particular binding affinity for hIL-18, the art-known method of surface plasmon resonance can be used. To select antibodies having a particular neutralizing activity for hIL-18, standard methods known in the art for assessing the inhibition of hIL-18 activity may be used. In addition, methods for immunizing mice that have been transgenically altered to encode a human immunoglobulin repertoire thereby enabling the organism to express fully human antibodies in response to an immunogen, are known in the art (see, e.g., U.S. Pat. Nos. 5,877,397 and 6,150,584).

Uses of Anti-IL-18 Antibodies

Given their ability to bind to hIL-18, the anti-hIL-18 antibodies, or portions thereof, of the invention can be used to detect hIL-18 (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting hIL-18 in a biological sample comprising contacting a biological sample with an antibody, or antibody portion, of the invention and detecting either the antibody (or antibody portion) bound to hIL-18 or unbound antibody (or antibody portion), to thereby detect hIL-18 in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$, $^{32}P$, $^{33}P$, or $^{3}H$.

Alternative to labeling the antibody, hIL-18 can be assayed in biological fluids by a competition immunoassay utilizing rhIL-18 standards labeled with a detectable substance and an unlabeled anti-hIL-18 antibody. In this assay, the biological sample, the labeled rhIL-18 standards and the anti-hIL-18 antibody are combined and the amount of labeled rhIL-18 standard bound to the unlabeled antibody is determined. The amount of hIL-18 in the biological sample is inversely proportional to the amount of labeled rhIL-18 standard bound to the anti-hIL-18 antibody.

The antibodies and antibody portions of the invention preferably are capable of neutralizing hIL-18 activity both in vitro and in vivo. Accordingly, such antibodies and antibody portions of the invention can be used to inhibit hIL-18 activity, e.g., in a cell culture containing hIL-18, in human subjects or in other mammalian subjects having IL-18 with which an antibody of the invention cross-reacts. In one embodiment, the invention provides a method for inhibiting IL-18 activity comprising contacting IL-18 with an antibody or antibody portion of the invention such that IL-18 activity is inhibited. Preferably, the IL-18 is human IL-18. For example, in a cell culture containing, or suspected of containing hIL-18, an antibody or antibody portion of the invention can be added to the culture medium to inhibit hIL-18 activity in the culture.

In another embodiment, the invention provides a method for inhibiting IL-18 activity in a subject suffering from a disorder in which IL-18 activity is detrimental. The invention provides methods for inhibiting IL-18 activity in a subject suffering from such a disorder, which method comprises administering to the subject an antibody or antibody portion of the invention such that IL-18 activity in the subject is inhibited. Preferably, the IL-18 is human IL-18 and the subject is a human subject. Alternatively, the subject can be a mammal expressing an IL-18 with which an antibody of the invention cross-reacts. Still further the subject can be a mammal into which has been introduced hIL-18 (e.g., by administration of hIL-18 or by expression of an hIL-18 transgene). An antibody of the invention can be administered to a human subject for therapeutic purposes. Moreover, an antibody of the invention can be administered to a non-human mammal expressing an IL-18 with which the antibody cross-reacts for veterinary purposes or as an animal model of human disease. Regarding the latter, such animal models may be useful for evaluating the therapeutic efficacy of antibodies of the invention (e.g., testing of dosages and time courses of administration).

In particular, one animal model for modulating IL-18 activity in an animal uses NOD-SCID mice which are transplanted with human peripheral blood mononuclear cells. Then, two to four weeks after engraftment (as measured by human IgG titers in serum) the mice are injected with LPS (lipopolysaccharide). Four to six hours later LPS-induced human interferon-gamma serum titers are determined. The efficacy (potency) of anti-IL-18 antibodies (e.g., IL-18 neutralizing antibodies) is determined by injecting the antibodies (ip) one day prior to LPS challenge followed by monitoring the test animals for a reduction in interferon-gamma serum titers (a function of IL-18 in vivo activity) as compared to controls (see, e.g., Holmes et al., Hybridoma, 19:363367 (2000)).

As used herein, the term "a disorder in which IL-18 activity is detrimental" is intended to include diseases and other disorders in which the presence of IL-18 in a subject suffering from the disorder has been shown to be, or is suspected of being, either responsible for the pathophysiology of the disorder or a factor that contributes to a worsening of the disorder. Accordingly, a disorder in which IL-18 activity is detrimental is a disorder in which inhibition of IL-18 activity is expected to alleviate the symptoms and/or progression of the disorder. Such disorders may be evidenced, for example, by an increase in the concentration of IL-18 in a biological fluid of a subject suffering from the disorder (e.g., an increase in the concentration of IL-18 in serum, plasma, synovial fluid, etc. of the subject), which can be detected, for example, using an anti-IL-18 antibody as described above.

Non-limiting examples of disorders that can be treated with the antibodies of the invention include those disorders discussed in the section above pertaining to pharmaceutical compositions of the antibodies of the invention.

Other features of the invention will be apparent from the following examples which should not be construed as limiting.

EXEMPLIFICATION

In general, the practice of the present invention employs, unless otherwise indicated, conventional techniques of chemistry, molecular biology, recombinant DNA technology, PCR technology, immunology (especially, e.g., antibody technology), and any necessary cell culture or animal husbandry techniques, which are within the skill of the art and are explained fully in the literature. See, e.g., Sambrook, Fritsch and Maniatis, *Molecular Cloning: Cold Spring Harbor Laboratory Press* (1989); *DNA Cloning*, Vols. 1 and 2, (D. N. Glover, Ed. 1985); *Oligonucleotide Synthesis* (M. J. Gait, Ed. 1984); *PCR Handbook Current Protocols in Nucleic Acid Chemistry*, Beaucage, Ed. John Wiley & Sons (1999) (Editor); *Oxford Handbook of Nucleic Acid Structure*, Neidle, Ed., Oxford Univ Press (1999); *PCR Protocols: A Guide to Methods and Applications*, Innis et al., Academic Press (1990); *PCR Essential Techniques: Essential Techniques*, Burke, Ed., John Wiley & Son Ltd (1996); *The PCR Technique: RT-PCR*, Siebert, Ed., Eaton Pub. Co. (1998); *Quantitative PCR Protocols*, Kochanowski et al., Eds., Humana Press (1999); *Clinical Applications of PCR*, Lo, Ed., Humana Press (1998); *Antibody Engineering Protocols (Methods in Molecular Biology)*, 510, Paul, S., Humana Pr (1996); *Antibody Engineering: A Practical Approach (Practical Approach Series, 169)*, McCafferty, Ed., In Pr (1996); *Antibodies: A Laboratory Manual*, Harlow et al., C.S.H.L. Press, Pub. (1999); *Current Protocols in Molecular Biology*, eds. Ausubel et al., John Wiley & Sons (1992); *Large-Scale Mammalian Cell Culture Technology*, Lubiniecki, A., Ed., Marcel Dekker, Pub., (1990); and *Manipulating the Mouse Embryo*, Hogan et al., C.S.H.L. Press, Pub (1994).

Throughout the examples, unless otherwise indicated, the above materials and methods were used.

Example 1

Isolation of Anti-IL-18 Antibodies

Antibodies to ML-18 were isolated by screening separate scFv phage display libraries prepared using human VL and VH cDNAs from mRNA derived from human B cells (e.g., tonsils and spleen). Construction of the library and methods for selection are described in Vaughan et al. (1996) *Nature Biotech.* 14: 309-314.

The libraries were screened using either full length human IL-18 (SEQ ID NO: 61), a peptide epitope of IL-18 (SEQ ID NOS: 1-3), or a panel of overlapping 15 amino acid peptides representing IL-18 (the epitope sequence of which is presented in Table 5; SEQ ID NOS: 31-60). IL-18 specific antibodies were selected by coating the antigen onto immunotubes using standard procedures (Marks et al., (1991) *J. Mol. Biol.* 222: 581-597). The scFv libraries were screened using either IL-18, a peptide epitope of IL-18, or an IL-18 peptide panel to generate a significant number of IL-18 specific binders. Several different clonotypes were selected, determined by restriction enzyme digestion patterns, and confirmed by DNA sequencing.

In order to identify IL-18 antibodies which preferentially bind either full length IL-18 or a representative peptide thereof, the supernatant containing scFv was titrated on biotin-captured IL-18 in an ELISA and binding characteristics were determined.

Two anti-IL-18 single chain antibodies were obtained, one termed 2E1, independently isolated using a peptide epitope and the peptide panel, and a second anti-IL-18 antibody termed LT28, isolated using full length IL-18. These parent anti-IL-18 antibodies were selected for further study and modification.

Example 2

Affinity Maturation of an Anti-18 Antibodies

A single chain Fv version of antibody 2E1 having an identified IL-18 binding activity and the heavy chain and light chain sequence shown in Table 6 was further modified for improved neutralization of IL-18 activity.

TABLE 6

Sequence of Single-Chain Anti-IL-18 Antibody 2E1

2E1 Heavy Chain
(SEQ ID NO: 18)

CDR1 (SEQ ID NO: 9)
QVQLVQSGAEVKKPGASMKVSCKTSGYTFTGYYIHWVRQAHGQGFEWI

CDR2 (SEQ ID NO: 10)   CDR3 (SEQ ID NO: 11)
GRLNPTTGDANFAEKFQGRVALTRDTSISTAYLQLDSLKSDDTAVYYCAGKEGAWGQGTLVTVSS

2E1 Light Chain
(SEQ ID NO: 19)

CDR1 (SEQ ID NO: 12)   CDR2 (SEQ ID NO: 13)
SSELTQDPAVSVALGQTVRITCQGDSLRHFYPNWYQQKPGQAPVLVIYGKNNRPS

CDR3 (SEQ ID NO: 14)
GIPDRFSGSGSGNTGSLTITGAQAEDEADYYCGSRDSSGIHVVFGGGTKVTVLG

The anti-IL-18 antibody 2E1 was independently selected using an IL-18 peptide and sequential, overlapping, peptide panel representative of IL-18 (see Table 6).

The specific amino acid residues of the heavy chain variable region selected for mutagenesis are summarized in Table 7. In particular, with respect to the heavy chain region, individual amino acid substitutions were tested at positions H30, H31, H32, H33, and H35 of CDR1, positions H52, H52a, H53, H54, H56, and H58 of CDR2, and H95, H96, H97, and H98 of CDR3.

With regards to light chain amino acid residues selected for mutagenesis, individual amino acid substitutions were tested at positions L30, L31, L32, and L34 of CDR1, positions L50, L52, L53, and L55 of CDR2 and positions L89, L90, L91, L92, L93, L94, L95, L95a, L95b, L96, and L97 of CDR 3.

TABLE 7

Heavy Chain Amino Acid Substitutions Introduced Into 2E1 Heavy Chain Mutations

| CDR/ Kabat Position | substituted residue |
|---|---|
| CDR1 | |
| H30 | A, R, N, D, C, G, H, I, F, P, S, or V |
| H31 | A, C, H, S, T, or Y |
| H32 | R, N, C, H, P, S, or T |
| H33 | N, D, C, Q, H, L, M, F, S, or V |
| H35 | N, D, L, or F |
| CDR2 | |
| H52 | T |
| H52a | R, Q, L, S, T, or W |
| H53 | A, R, N, L, P, S, or Y |
| H54 | A, R, N, D, Q, L, K, M, P, S, or Y |
| H56 | A, R, N, C, G, H, I, L, or F |
| H58 | A, R, Q, E, H, I, L, K, M, F, S, T, Y, P, S, T, W, Y, or V |
| CDR3 | |
| H95 | A, R, E, Q, S, Y, V, H, P, W, or C |
| H96 | A, R, Q, S, Y, V, H, P, W, or C |
| H97 | A, R, E, Q, S, Y, V, H, P, W, or C |
| H98 | R, E, Q, S, Y, V, H, P, W, or C |

TABLE 8

Light Chain Amino Acid Substitutions Introduced Into 2E1 Light Chain Mutations

| CDR/ Kabat Position | substituted residue |
|---|---|
| CDR1 | |
| L30 | N, D, C, G, I, L, S, W, or Y |
| L31 | R, N, D, C, G, H, I, L, P, S, T, or Y |
| L32 | R, N, D, E, G, I, L, P, S, T, or V |
| L34 | A, R, N, D, E, H, I, L, K, M, F, P, S, T, Y, or V |
| CDR2 | |
| L50 | A, N, I, L, F, P, S, W, Y, or V |
| L52 | A, R, D, E, H, I, L, M, F, P, S, T, or V |
| L53 | A, R, C, I, L, K, M , P, S, or T |
| L55 | A, R, N, D, C, G, H, I, L, S, T, or Y |
| CDR3 | |
| L89 | A, R, E, Q, S, Y, V, H, P, W, or C |
| L90 | A, R, E, Q, Y, V, H, P, W, or C |
| L91 | R, E, Q, S, Y, V, H, P, W, or C |
| L92 | A, R, E, Q, S, Y, V, H, P, W, or C |
| L93 | A, R, E, Q, Y, V, H, P, W, or C |
| L94 | A, R, E, Q, Y, V, H, P, W, or C |
| L95 | A, R, E, Q, S, Y, V, H, P, W, or C |
| L95a | A, R, E, Q, S, Y, V, H, P, W, or C |
| L95b | A, R, E, Q, S, Y, V, P, W, or C |
| L96 | A, R, E, Q, S, Y, H, P, W, or C |
| L97 | A, R, E, Q, S, Y, H, P, W, or C |

Substitutions were introduced using standard techniques (e.g., as described in Taylor et al., *Nucleic Acids Res.* 13: 8764-8758 (1985); Nakamaye et al., *Nucleic Acids Res.* 14: 9679-9698 (1986); and Olsen et al., *Methods in Enzymology*, 217: 189 (1993)). In brief, oligonucleotides degenerate for a given codon were synthesized for each of the positions to be mutagenized. A single-stranded DNA template was prepared from the original plasmid containing a single-chain Fv version of the antibody 2E1 gene. The nucleic acid sequence of the parent 2E1 antibody heavy and light chain is provided in SEQ ID NOS: 62 and 64. The mutant oligonucleotides were then used to create a complementary DNA strand and eventually a double-stranded plasmid, thus incorporating the degeneracy or the different mutations in a given codon of the antibody. In particular, the CDR3 region of the heavy and light chain of 2E1 was altered using the QuikChange Kit (Stratagene) according to the manufactures instruction.

A representative number of clones were then sequenced from each mutagenesis reaction (i.e., 7 to 36 clones) and those representing a change from the parent 2E1 single chain antibody sequence were expressed in bacteria and purified for further in vitro and in vivo testing as described infra.

In another screen using a full length IL-18 ligand, a second anti-IL-18 antibody was identified and selected for further improvement using affinity maturation. In particular, using the techniques described above, the LT28 antibody having the heavy chain and light chain sequence shown in Table 9 (and nucleic sequence provided in SEQ ID NOS: 66 and 68) was further modified.

TABLE 9

Sequence of Single-Chain Anti-IL-18 Antibody LT28

LT28 Heavy Chain
(SEQ ID NO: 28)

CDR1 (SEQ ID NO: 20)   CDR2 (SEQ ID NO: 21)
LVQPGGSLRLSCAASGFTFSSYAMSWVRQAPGKGLEWVSAISGSGGSTYYADSVKG

CDR3 (SEQ ID NO: 22)
RFTISRDNSKNTLYLQMNSLRAEDTAVYYCARDDDDYDFDYWGRGTMVTVSS

LT28 Light Chain
(SEQ ID NO: 29)

CDR1 (SEQ ID NO: 23)          CDR2 (SEQ ID NO: 24)
QSVLTQPPSASGTPGQRVTISCSGSSSNIGINAVNWYQQLPGTAPKLLIYGNDQRPS

CDR3 (SEQ ID NO: 25)
GVPDRFSGSKSGTSASLAISGLQSEDEADYYCAAWDDSLSGPVFGGGTKLTVLG

With respect to the heavy chain region, amino acid substitutions were introduced at positions I131, H32, I133, and H35 of CDR1, positions I150, I451, H52, H52a, H53, H54, H56, and H58 of CDR2, and H95, H96, H97, H98, H99, H100, H100a, H101, and H102 of CDR3.

With regards to light chain residues selected for mutation, amino acid substitutions were introduced at positions L30, L31, L32, L34 of CDR1, positions L50, L52, L53, L55 of CDR2 and positions L89, L90, L91, L92, L93, L94, L95, L95a, L95b, L96, L97.

TABLE 10

Heavy Chain Amino Acid Substitutions
Introduced into LT28
Heavy Chain Mutations

| CDR/Kabat Position | substituted residue |
|---|---|
| CDR1 | |
| H31 | A, R, E, Q, S, Y, V, H, P, W, or C |
| H32 | A, R, E, Q, S, Y, V, H, P, W, or C |
| H33 | A, R, E, Q, S, Y, V, H, P, W, or C |
| H35 | A, R, E, Q, S, Y, V, H, P, W, or C |
| CDR2 | |
| H50 | A, R, E, Q, S, Y, V, H, P, W, or C |
| H51 | A, R, E, Q, S, Y, V, H, P, W, or C |
| H52 | A, R, E, Q, S, Y, V, H, P, W, or C |
| H52a | A, R, E, Q, S, Y, V, H, P, W, or C |
| H53 | A, R, E, Q, S, Y, V, H, P, W, or C |
| H54 | A, R, E, Q, S, Y, V, H, P, W, or C |
| H56 | A, R, E, Q, S, Y, V, H, P, W, or C |
| H58 | A, R, E, Q, S, Y, V, H, P, W, C |

TABLE 10-continued

Heavy Chain Amino Acid Substitutions
Introduced into LT28
Heavy Chain Mutations

| CDR/Kabat Position | substituted residue |
|---|---|
| CDR3 | |
| H95 | A, R, E, Q, S, Y, V, H, P, W, or C |
| H96 | A, R, E, Q, S, Y, V, H, P, W, or C |
| H97 | A, R, E, Q, S, Y, V, H, P, W, or C |
| H98 | A, R, E, Q, S, Y, V, H, P, W, or C |
| H99 | A, R, E, Q, S, Y, V, H, P, W, or C |
| H100 | A, R, E, Q, S, Y, V, H, P, W, or C |
| H100a | A, R, E, Q, S, Y, V, H, P, W, or C |
| H101 | A, R, E, Q, S, Y, V, H, P, W, or C |
| H102 | A, R, E, Q, S, Y, V, H, P, W, or C |

TABLE 11

Light Chain Amino Acid Substitutions
Introduced into LT28
Light Chain Mutations

| CDR/Position | substituted residue |
|---|---|
| CDR1 | |
| L30 | A, R, E, Q, S, Y, V, H, P, W, C |
| L31 | A, R, E, Q, S, Y, V, H, P, W, C |
| L32 | R, E, Q, S, Y, V, H, P, W, C, G |
| L34 | A, R, E, Q, S, Y, V, H, P, W, C |
| CDR2 | |
| L50 | A, R, E, Q, S, Y, V, H, P, C |
| L52 | A, R, E, S, Y, V, H, P, W, C |

TABLE 11-continued

Light Chain Amino Acid Substitutions
Introduced into LT28
Light Chain Mutations

| CDR/Position | substituted residue |
|---|---|
| L53 | A, R, E, S, Y, V, H, P, W, C, N |
| L55 | A, E, Q, S, Y, V, H, P, W, C |
| CDR3 | |
| L89 | A, R, E, Q, S, Y, V, H, P, W, C |
| L90 | A, R, E, Q, S, Y, V, H, P, W, C |
| L91 | A, R, E, Q, S, Y, V, H, P, W, C |
| L92 | A, R, E, Q, S, Y, V, H, P, W, C |
| L93 | A, R, E, Q, S, Y, V, H, P, W, C |
| L94 | A, R, E, Q, S, Y, V, H, P, W, C |
| L95 | A, R, E, Q, S, Y, V, H, P, W, C |
| L95a | A, R, E, Q, S, Y, V, H, P, W, C |
| L95b | A, R, E, Q, S, Y, V, H, P, W, C |
| L96 | A, R, E, Q, S, Y, V, H, P, W, C |
| L97 | A, R, E, Q, S, Y, V, H, P, W, C |

Substitutions were introduced as described above. A representative number of clones were then sequenced from each mutagenesis reaction and those representing a change from the parent LT28 single chain antibody sequence were expressed in bacteria and purified for further testing as described below.

Example 3

Binding Activity of Human Antibodies to IL-18

Real-time binding interactions between ligand (biotinylated recombinant human IL-18 (rhIL-18) immobilized on a biosensor matrix) and analyte (antibodies in solution) were measured by surface plasmon resonance (SPR) using the BIAcore system (Pharmacia Biosensor, Piscataway, N.J.). The system utilizes the optical properties of SPR to detect alterations in protein concentrations within a dextran biosensor matrix. Proteins are covalently bound to the dextran matrix at known concentrations. Antibodies are injected through the dextran matrix and specific binding between injected antibodies and immobilized ligand results in an increased matrix protein concentration and resultant change in the SPR signal. These changes in SPR signal are recorded as resonance units (RU) and are displayed with respect to time along the y-axis of a sensorgram.

To facilitate immobilization of biotinylated rhIL-18 on the biosensor matrix, streptavidin is covalently linked via free amine groups to the dextran matrix by first activating carboxyl groups on the matrix with 100 mM N-hydroxysuccinimide (NHS) and 400 mM N-ethyl-N'-(3-diethylaminopropyl)carbodiimide hydrochloride (EDC). Next, streptavidin is injected across the activated matrix. Thirty-five microliters of streptavidin (25 µg/ml), diluted in sodium acetate, pH 4.5, is injected across the activated biosensor and free amines on the protein are bound directly to the activated carboxyl groups. Unreacted matrix EDC-esters are deactivated by an injection of 1 M ethanolamine. Streptavidin-coupled biosensor chips also are commercially available (Pharmacia BR-1000-16, Pharmacia Biosensor, Piscataway, N.J.).

Biotinylated rhIL-18 was prepared by first dissolving 5.0 mg of biotin (D-biotinyl-ε-aminocaproic acid N-hydroxysuccinimide ester; Boehringer Mannheim Cat. No. 1008 960) in 500 µl dimethylsulfoxide to make a 10 mg/ml solution. Ten microliters of biotin was added per ml of rhIL-18 (at 2.65 mg/ml) for a 2:1 molar ratio of biotin to rhIL-18. The reaction was mixed gently and incubated for two hours at room temperature in the dark. A PD-10 column, Sephadex G-25M (Pharmacia Catalog No. 17-0851-01) was equilibrated with 25 ml of cold PBS and loaded with 2 ml of rhIL-18-biotin per column. The column was eluted with 10×1 ml cold PBS. Fractions were collected and read at OD280 (1.0 OD=1.25 mg/ml). The appropriate fractions were pooled and stored at −80° C. until use.

Biotinylated rhIL-18 to be immobilized on the matrix via streptavidin was diluted in PBS running buffer (Gibco Cat. No. 14190-144, Gibco BRL, Grand Island, N.Y.) supplemented with 0.05% (BIAcore) surfactant P20 (Pharmacia BR-1000-54, Pharmacia Biosensor, Piscataway, N.J.). To determine the capacity of rhIL-18-specific antibodies to bind immobilized rhIL-18, a binding assay was conducted as follows. Aliquots of biotinylated rhIL-18 (25 nM; 10 µl aliquots) were injected through the streptavidin-coupled dextran matrix at a flow rate of 5 µl/min. Before injection of the protein and immediately afterward, PBS buffer alone flowed through each flow cell. The net difference in signal between baseline and approximately 30 sec. after completion of biotinylated rhIL-18 injection was taken to represent the binding value. Direct rhIL-18-specific antibody binding to immobilized biotinylated rhIL-18 was measured. Antibodies (20 µg/ml) were diluted in PBS running buffer and 25 µl aliquots were injected through the immobilized protein matrices at a flow rate of 5 µl/min. Prior to injection of antibody, and immediately afterwards, PBS buffer alone flowed through each flow cell. The net difference in baseline signal and signal after completion of antibody injection was taken to represent the binding value of the particular sample. Biosensor matrices were regenerated using 100 mM HCl before injection of the next sample. To determine the off rate ($K_{off}$), on rate ($K_{on}$), association rate ($K_a$) and dissociation rate ($K_d$) constants, BIAcore kinetic evaluation software (version 2.1) was used.

Representative results of improved candidate anti-IL-18 antibodies binding to biotinylated rhIL-18, as compared to the parent antibodies 2E1 and LT28 (and murine controls), are shown below in Table 12. For comparison, IC50 values from the cell-based neutralization assay are also included and these are described in Example 4. All clones were prepared as single-chain Fv antibodies for testing using Biacore analysis and the cell-based assay described below. Parental clones listed comprise an unmutated parental heavy and light chain, whereas single chain mutants contain one parental chain and one mutated chain where the mutated chan is indicated as being either heavy (H) or light (L) followed by the Kabat position and nature of the amino acid substitution.

TABLE 12

Binding of Anti-IL-18 Antibodies Derived From 2E1 and LT28

| Antibody Clone | On-rates ($M^{-1}s^{-1}$) | Off-rates ($s^{-1}$) | Kd (M) | IC50 Value* |
|---|---|---|---|---|
| 2E1 parent and mutants | | | | |
| 2E1 (parent) ScFv | 2.6E+3 | 6.42E−03 | 1.5E−07 | 3.3E−8M |
| 2E1 (parent) IgG | | | | 9.0E−10M |
| L34S | | 1.69E−04 | | 1.5E−8M |
| H53R | | 2.34E−03 | | 2.5E−8M |
| H53Y | | — | | 1.5E−8M |
| H58Q | | — | | 1.6E−8M |
| L34S + H53R (2E1RS) | 2.7E+03 | 6.82E−05 | 2.3E−08 | 3.0E−09M |
| L34S + H58Q | | — | | 1.5E−8M |
| L34S + H53Y | | 5.28E−05 | | 6.7E−9M |
| H53R + H58Q | | — | | 1.2E−8M |

TABLE 12-continued

Binding of Anti-IL-18 Antibodies Derived From 2E1 and LT28

| Antibody Clone | On-rates $(M^{-1}s^{-1})$ | Off-rates $(s^{-1})$ | Kd (M) | IC50 Value* |
|---|---|---|---|---|
| H53Y + H58Q | — | | | 1.2E-8M |
| L34S + H53R + H58Q | | 6.18E-05 | | 2.8E-9M |
| L34S + H53Y + H58Q | — | | | 8.0E-9M |
| L90C | | | | 4x |
| L93C | | | | 2-4x |
| L94P, Q, or R | | | | 2-4x |
| L95R, Y | | | | 3-8x |
| L95bE,W | | | | 2-4x |
| LT28 parent and mutants | | | | |
| LT28 (parent) | 1.3E+04 | 4.8E-04 | 3.9E-08 | 9.0E-8M |
| H54Q | | | | 2-3x |
| H58W | | | | 2-3x |
| 1 | | | | |
| 125-2H | 1.7E+05 | 1.1E-04 | 6.2E-10 | 2.E-10M |
| 318-M | 1.2E+04 | 1.1E-04 | 9.6E-09 | 4.0E-9M |

*Some values presented as fold improvement compared to the parent.

Example 4

Neutalizing Activity of Anti-IL-18 Antibodies

To examine the neutralizing activity of the anti-human IL-18 antibodies of the invention, an art recognized assay for monitoring IL-18 activity was used.

Briefly, the assay employs KG1 cells (ATCC #CCL-246, myelogenous leukemia bone marrow cells) which were cultured according to standard techniques (e.g., using RPMI 1640 Culture Medium Gibco #21870-076; (supplemented with 10% Fetal Bovine Serum (BioWhittaker #14-501F); 2 mM L-glutamine (Gibco #25030-081); 50 units/ml Penicillin, 50 ug/ml Streptomycin (Gibco #15070-063); and 0.075% Sodium Bicarbonate).

To test for IL-18 neutralization, 3×10E5 KG-1 cells stimulated with 20 ng/ml hTNF-alpha (Lot# 19130132) was incubated with 50 ul of anti-IL-18 antibody (4×Conc.) and 50 ul of IL-18 (4×Conc.=8 ng/ml) and incubated for 37° C. for 1 hr or 16-20 hrs. To determine the amount of IL-18 neutralization that occurred as a function of induced hIFN-gamma production, an ELISA was performed using commercially available Elisa Kits (R & D #DIF00/Endogen #EH-IFNG), according to the manufacturers instructions, and hIFN-gamma production was calculated (pg/ml) off a standard curve.

In all, four mutant antibodies, i.e., the 2E1 derived L34S, H53R, H53Y, and H58Q, were shown to have greater IL-18 neutralization potency than the parent 2E1 antibody (see Table 12). The improvements in IC50 values using the KG-1 assay were in the range of 2 to 5 fold, and similar improved binding results were determined using BIAcore analysis.

Various mutation combination clones were also prepared and tested, and this data is summarized in the Table 12. The best combination clone L34S-H53R showed a greater than ten fold improvement over the parent antibody 2E1 in both the KG-1 cell-based assay and using the BIAcore analysis. The resulting antibody was designated the name of 2E1RS.

Several other mutant clones of 2E1 showed an improvement in potency, i.e., IL-18 neutralization, as determined using the KG-1 assay. The mutant L95Y offered 5 to 8 fold better IC50 values than the parent 2E1 antibody. Several other mutants offered a 2 to 3 fold improvement and they are 2E1 mutants H96A, H96Q, H96S, H98S, L90C, L90W, L93C, L94P, L94P, L94Q, L94R, L94W, L95R, L95aA, L95aH, L95aP, L95aR, L95aW, L95bE, L95bW, L95bY, L97C, and L97E.

Figure 5:
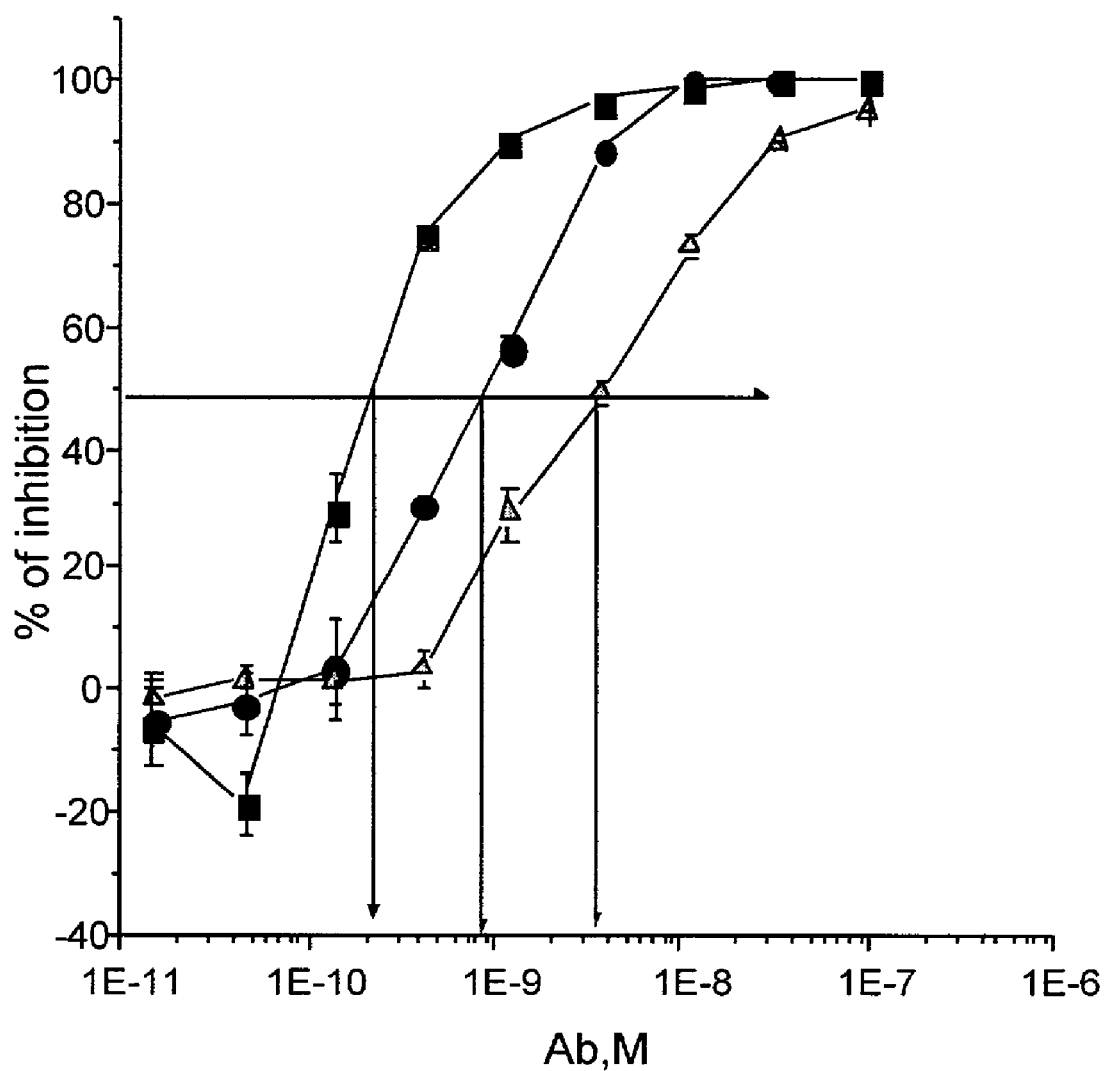
FIG. 5 shows the potency of three different anti-IL-18 antibodies in neutralizing the biologic effects of IL-18 as a function of inhibition of IFN-γ induction in KG1 cells. The IC50 values for the antibodies 125H (boxes) and the 2E1 antibody as an IgG antibody (circles) or as a single chain antibody (triangles) are, respectively, 2.1E-10, 9.0E-10, and 3.3E-9.

The binding of 2E1 in the form of an ScFv antibody or IgG antibody was also compared (see FIG. 5).

Still further, two mutants derived from the LT28 parent should improved 1L-18 neutralization activity compared to the parent antibody.

These results demonstrate that fully human IL-18 neutralizing antibodies can be obtained using the methods and compositions of the invention.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated antibody, or an antigen-binding portion thereof, capable of binding human IL-18, wherein said antibody or antigen-binding portion thereof comprises a heavy chain variable region comprising a CDR1, a CDR2, and a CDR3 domain selected from the group consisting of:

a heavy chain CDR1 domain of SEQ ID NO: 9 or modified from SEQ ID NO: 9 by at least one amino acid substitution at a position selected from the group consisting of H30, H31, H32, H33, and H35, wherein the amino acid substitution at H30 is selected from the group consisting of A, R, N, D, C, G, H, I, F, P, S, and V; wherein the amino acid substitution at H31 is selected from the group consisting of A, C, H, S, T, and Y; wherein the amino acid substitution at H32 is selected from the group consisting of R, N, C, H, P, S, and T; wherein the amino acid substitution at H33 is selected from the group consisting of N, D, C, Q, H, L, M, F, S, and V; and wherein the amino acid substitution at H34 is selected from the group consisting of N, D, L, and F;

a heavy chain CDR2 domain of SEQ ID NO: 10 or modified from SEQ ID NO: 10 by at least one amino acid substitution at a position selected from the group consisting of H52, H52a, H53, H54, H56, and H58, wherein the amino acid substitution at H52 is T; wherein the amino acid substitution at H52a is selected from the group consisting of R, Q, L, S, T and W; wherein the amino acid substitution at H53 is selected from the group consisting of A, R, N, L, P, S, and Y; wherein the amino acid substitution at H54 is selected from the group consisting of A, R, N, D, Q, L, K, M, P, S, and Y; wherein the amino acid substitution at H56 is selected from the group consisting of A, R, N, C, G, H, I, L, and F; and wherein the amino acid substitution at H58 is selected from the group consisting of A, R, Q, E, H, I, L, K, M, F, S, T, Y, P, S, T, W, Y, and V; and a heavy chain CDR3 domain of SEQ ID NO: 11 or modified from SEQ ID NO: 11 by at least one amino acid substitution at a position selected from the group consisting of H95, H96, H97, and H98, wherein the amino acid substitution at H95 is A, R, E, Q, S, Y, V, H, P, W, and C; wherein the amino acid substitution at H96 is selected from the group consisting of A, R, Q, S, Y, V, H, P, W and C; wherein the amino acid substitution at H97 is selected from the group consisting of A, R, E, Q, S, Y, V, H, P, W, and C; and wherein the amino acid substitution at H98 is selected from the group consisting of R, E, Q, S, Y, V, H, P, W, and C; and wherein said antibody or antigen-binding portion thereof comprises a light chain variable region comprising a CDR1, a CDR2, and a CDR3 domain selected from the group consisting of:

a light chain CDR1 domain of SEQ ID NO: 12 or modified from SEQ ID NO: 12 by at least one amino acid substitution at a position selected from the group consisting of L30, L31, L32, and L34, wherein the amino acid substitution at L30 is selected from the group consisting of N, D, C, G, I, L, S, W, and Y; wherein the amino acid substitution at L31 is selected from the group consisting of R, N, D, C, G, H, I, L, P, S, T, and Y; wherein the amino acid substitution at L32 is selected from the group consisting of R, N, D, E, G, I, L, P, S, T, and V; and wherein the amino acid substitution at L34 is selected from the group consisting of A, R, N, D, E, H, I, L, K, M, F, P, S, T, Y and V;

a light chain CDR2 domain of SEQ ID NO: 13 or modified from SEQ ID NO: 13 by at least one amino acid substitution at a position selected from the group consisting of L50, L52, L53, and L55, wherein the amino acid substitution at L50 is A, N, I, L, F, P, S, W, Y and V; wherein the amino acid substitution at L52 is selected from the group consisting of A, R, D, E, H, I, L, M, F, P, S, T, and V; wherein the amino acid substitution at L53 is selected from the group consisting of A, R, C, I, L, K, M, P, S and T; wherein the amino acid substitution at L55 is selected from the group consisting of A, R, N, D, C, G, H, I, L, S, T, and Y; and a light chain CDR3 domain of SEQ ID NO: 14 or modified from SEQ ID NO: 14 by at least one amino acid substitution at a position selected from the group consisting of L89, L90, L91, L92, L93, L94, L95, L95a, L95b, L96, and L97, wherein the amino acid substitution at L89 is A, R, E, Q, S, Y, V, H, P, W, and C; wherein the amino acid substitution at L90 is selected from the group consisting of A, R, E, Q, Y, V, H, P, W and C; wherein the amino acid substitution at L91 is selected from the group consisting of R, E, Q, S, Y, V, H, P, W, and C; and wherein the amino acid substitution at L92 is selected from the group consisting of A, R, E, Q, S, Y, V, H, P, W, and C; wherein the amino acid substitution at L93 is A, R, E, Q, Y, V, H, P, W, and C; wherein the amino acid substitution at L94 is selected from the group consisting of A, R, E, Q, Y, V, H, P, W and C; wherein the amino acid substitution at L95 is selected from the group consisting of A, R, E, Q, S, Y, V, H, P, W, and C; and wherein the amino acid substitution at L95a is selected from the group consisting of A, R, E, Q, S, Y, V, H, P, W, and C; wherein the amino acid substitution at L95b is A, R, E, Q, S, Y, V, P, W, and C; wherein the amino acid substitution at L96 is selected from the group consisting of A, R, E, Q, S, Y, H, P, W and C; and wherein the amino acid substitution at L97 is selected from the group consisting of A, R, E, Q, S, Y, H, P, W, and C; wherein the at least one amino acid substitution does not inhibit IL-18 binding to the epitope comprising an amino acid sequence selected from the group consisting of SEQ ID NO: 3 and SEQ ID NO: 36.

2. An isolated antibody, or an antigen-binding portion thereof, comprising one heavy chain variable region and one light chain variable region, at least one of said variable regions comprising an amino acid sequence selected from the group consisting of SEQ ID NO: 15, 16, and 17, wherein said isolated human antibody, or said antigen-binding portion thereof is capable of binding human IL-18.

3. An isolated antibody, or an antigen-binding portion thereof, comprising a light chain variable region (LCVR) having an amino acid sequence of SEQ ID NO: 15 and a heavy chain variable region (HCVR) having an amino acid sequence of SEQ ID NO: 16, wherein said isolated human antibody, or said antigen-binding portion thereof is capable of binding human IL-18.

4. An isolated antibody, or an antigen-binding portion thereof, comprising a light chain variable region (LCVR) having the amino acid sequence of SEQ ID NO: 15 and a heavy chain variable region (HCVR) having the amino acid sequence of SEQ ID NO: 17, wherein said isolated human antibody, or said antigen-binding portion thereof is capable of binding human IL-18.

5. An isolated antibody, or an antigen-binding portion thereof, capable of binding human IL-18, wherein said antibody or antigen-binding portion thereof comprises a heavy chain variable region comprising a CDR1, a CDR2, and a CDR3 domain selected from the group consisting of:

a heavy chain CDR1 domain of SEQ ID NO: 20 or modified from SEQ ID NO: 20 by at least one amino acid substitution at a position selected from the group consisting of H31, H32, H33, and H35;

a heavy chain CDR2 domain of SEQ ID NO: 21 or modified from SEQ ID NO: 21 by at least one amino acid substitution at a position selected from the group consisting of H50, H51, H52, H52a, H53, H54, H56, and H58; and a heavy chain CDR3 domain of SEQ ID NO: 22 or modified from SEQ ID NO: 22 by at least one amino acid substitution at a position selected from the group consisting of H95, H96, H97, H98, H99, H100, H100a, H101, and H102, wherein the at least one amino acid substitution is selected from the group consisting of A, R, E, Q, S, Y, V, H, P, W and C; and wherein said antibody or antigen-binding portion thereof comprises a light chain variable region comprising a CDR1, a CDR2, and a CDR3 domain selected from the group consisting of:

a light chain CDR1 domain of SEQ ID NO: 23 or modified from SEQ ID NO: 23 by at least one amino acid substitution at a position selected from the group consisting of L30, L31, L32, and L34, wherein said substitution in L30 is selected from the group consisting of A, R, E, Q, S, Y, V, H, P, W and C; wherein said substitution in L31 is selected from the group consisting of A, R, E, Q, S, Y, V, H, P, W and C; wherein said substitution in L32 is selected from the group consisting of R, E, Q, S, Y, V, H, P, W C, and G; and wherein said substitution in L34 is selected from the group consisting of A, R, E, Q, S, Y, V, H, P, W and C;

a light chain CDR2 domain of SEQ ID NO: 24 or modified from SEQ ID NO: 24 by at least one amino acid substitution at a position selected from the group consisting of L50, L52, L53, and L55, wherein said substitution in L50 is selected from the group consisting of A, R, E, Q, S, Y, V, H, P, W and C; wherein said substitution in L52 is selected from the group consisting of A, R, E, S, Y, V, H, P, W, and C; wherein said substitution in L53 is selected from the group consisting of A, R, E, S, Y, V, H, P, W C, and N; and wherein said substitution in L54 is selected from the group consisting of A, E, Q, S, Y, V, H, P, W and C; and a light chain CDR3 domain of SEQ ID NO: 25 or modified from SEQ ID NO: 25 by at least one amino acid substitution at a position selected from the group consisting of L89, L90, L91, L92, L93, L94, L95, L95a, L95b, L96, and L97, wherein said substitution is selected from the group consisting of A, R, E, Q, S, Y, V, H, P, W, and C; wherein the at least one amino acid substitution does not inhibit IL-18 binding to the epitope comprising an amino acid sequence selected from the group consisting of SEQ ID NO: 33.

6. An isolated antibody, or an antigen-binding portion thereof, comprising one heavy chain variable region and one light chain variable region, at least one of said variable regions comprising an amino acid selected from the group consisting of SEQ ID NO: 26, 27, and 29.

7. An isolated antibody, or an antigen-binding portion thereof, comprising a light chain variable region (LCVR) comprising the amino acid sequence of SEQ ID NO: 29 and a heavy chain variable region (HCVR) comprising the amino acid sequence of SEQ ID NO: 26, wherein said isolated human antibody, or said antigen-binding portion thereof is capable of binding human IL-18.

8. An isolated antibody, or an antigen-binding portion thereof, comprising a light chain variable region (LCVR) having the amino acid sequence of SEQ ID NO: 29 and a heavy chain variable region (HCVR) having the amino acid sequence of SEQ ID NO: 27, wherein said isolated human antibody, or said antigen-binding portion thereof is capable of binding human IL-18.

9. A method for inhibiting human IL-18 activity comprising contacting human IL-18 with the antibody, or an antigen-binding portion thereof, of any one of claims 1, 2-4, 5 and 6-8, such that human IL-18 activity is inhibited.

10. A method for inhibiting human IL-18 activity comprising contacting human IL-18 with the antibody, or antigen-binding portion thereof, of any of claims 1, 2-4, 5 and 6-8, such that human IL-18 activity is inhibited.

11. A method for inhibiting human IL-18 activity in a human subject suffering from a disorder in which IL-18 activity is detrimental, comprising administering to the human subject the antibody, or an antigen-binding portion thereof, of any one of claims 1, 2-4, 5 and 6-8, such that human IL-18 activity in the human subject is inhibited.

12. A method for inhibiting human IL-18 activity in a human subject suffering from a disorder in which IL-18 activity is detrimental, comprising administering to the human subject the antibody, or antigen-binding portion thereof, of any of claims 1, 2-4, 5 and 6-8, such that human IL-18 activity in the human subject is inhibited.

13. A method for inhibiting human IL-18 activity in a human subject suffering from a disorder in which IL-18 activity is detrimental by administering the antibody, or an antigen-binding portion thereof, of any one of claims 1, 2-4, 5 and 6-8, such that said inhibiting is achieved.

14. A method for inhibiting human IL-18 activity in a human subject suffering from a disorder in which IL-18 activity is detrimental by administering an antibody, or antigen-binding portion thereof, of any one of claims 1, 2-4, 5 and 6-8, such that said inhibiting is achieved.

15. The method of claim 13 or 14, wherein said disorder is selected from the group comprising rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency, common variable hypogammaglobulinaemia, dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjören's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis, classical autoimmune or lupoid hepatitis, type-2 autoimmune hepatitis, anti-LKM antibody hepatitis, autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, all subtypes of multiple sclerosis, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjören's syndrome, Takayasu's disease/arteritis, autoimmune thrombocytopaenia, idiopathic thrombocytopaenia, autoimmune thyroid disease, hyperthyroidism, goitrous autoimmune hypothyroidism or Hashimoto's disease, atrophic autoimmune hypothyroidism, primary myxoedema, phacogenic uveitis, primary vasculitis, vitiligo, acute liver disease, chronic liver diseases, allergy and asthma, mental disorders, depression, schizophrenia, and Th2 Type and Th1 Type mediated diseases.

16. A method of inhibiting human IL-18 activity in a patient suffering from a disorder in which IL-18 is detrimental comprising the step of administering the anti-IL-18 antibody, or antigen-binding portion thereof according to any one of claims 1, 2-4, 5 and 6-8, before, concurrent, or after the administration of a second agent, wherein the second agent is selected from the group consisting of an anti-IL-12 antibody or antigen binding fragment thereof, methotrexate, anti-TNF antibody or antigen binding fragment thereof, corticosteroids, cyclosporin, rapamycin, FK506, and non-steroidal anti-inflammatory agents.

* * * * *